US012636154B2

(12) United States Patent
Griswold et al.

(10) Patent No.: US 12,636,154 B2
(45) Date of Patent: May 26, 2026

(54) TRANSCATHETER VALVE DELIVERY SYSTEM WITH OMNIDIRECTIONAL STEERING AND METHODS OF USE THEREOF

(71) Applicant: Medtronic, Inc., Minneapolis, MN (US)

(72) Inventors: Erik Griswold, Pennegrove, CA (US); Joshua Dwork, Santa Rosa, CA (US); Jamie Dunaway, Santa Rosa, CA (US); Finn Rinne, Santa Rosa, CA (US); Nathan Wiemeyer, Windsor, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 947 days.

(21) Appl. No.: 17/828,389

(22) Filed: May 31, 2022

(65) Prior Publication Data

US 2023/0016149 A1 Jan. 19, 2023

Related U.S. Application Data

(60) Provisional application No. 63/222,571, filed on Jul. 16, 2021, provisional application No. 63/222,583, filed on Jul. 16, 2021.

(51) Int. Cl.
*A61F 2/24* (2006.01)
*A61F 2/95* (2013.01)
(Continued)

(52) U.S. Cl.
CPC .......... *A61F 2/2466* (2013.01); *A61F 2/2418* (2013.01); *A61F 2/2436* (2013.01);
(Continued)

(58) Field of Classification Search
CPC . A61F 2/2427–2/2439; A61M 25/0138; A61B 2017/003
See application file for complete search history.

(56) References Cited

U.S. PATENT DOCUMENTS 6,607,496 B1 8/2003 Poor et al.
9,034,032 B2 5/2015 Mclean et al.
(Continued)

FOREIGN PATENT DOCUMENTS

WO 2011035327 A1 3/2011
WO WO-2012139869 A2 * 10/2012 ......... A61B 1/00071
(Continued)

OTHER PUBLICATIONS

International Search Report and Written Opinion issued Dec. 5, 2022 in International Appl. No. PCT/IB2022/056428.

*Primary Examiner* — Alvin J Stewart
(74) *Attorney, Agent, or Firm* — MEDLER FERRO WOODHOUSE & MILLS PLLC

(57) ABSTRACT

A delivery system for prosthetic heart valves are provided. The delivery system includes a flexible shaft, a distal sheath capsule configured to contain the prosthetic heart valve, an inner steerable catheter including an inner distal flex component, and an outer steerable catheter including an outer distal flex component. The inner distal flex component includes a first cut pattern and a second cut pattern distal to the first cut pattern. The outer distal flex component includes a third cut pattern. The inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

20 Claims, 26 Drawing Sheets

(51) Int. Cl.
    *A61M 25/01*      (2006.01)
    *A61B 17/00*      (2006.01)

(52) U.S. Cl.
    CPC ....... *A61F 2/9517* (2020.05); *A61M 25/0147*
    (2013.01); *A61B 2017/00243* (2013.01); *A61F*
    *2230/0054* (2013.01)

(56)           References Cited

U.S. PATENT DOCUMENTS

| | | | |
|---|---|---|---|
| 10,188,833 B2 | 1/2019 | Bolduc et al. | |
| 10,278,852 B2 * | 5/2019 | Griffin | A61F 2/966 |
| 10,561,497 B2 | 2/2020 | Duffy et al. | |
| 10,799,224 B2 * | 10/2020 | Tasci | A61B 17/00234 |
| 11,318,013 B2 | 5/2022 | Mcveigh et al. | |
| 12,090,051 B2 * | 9/2024 | Crosbie | A61F 2/966 |
| 12,245,942 B2 * | 3/2025 | Siegel | A61F 2/2427 |
| 2006/0265056 A1 | 11/2006 | Nguyen et al. | |
| 2007/0239266 A1 | 10/2007 | Birdsall | |
| 2007/0239269 A1 | 10/2007 | Dolan et al. | |
| 2012/0035722 A1 | 2/2012 | Tuval | |
| 2012/0101572 A1 | 4/2012 | Kovalsky et al. | |
| 2012/0323077 A1 * | 12/2012 | Verbeek | A61B 1/0055 |
| | | | 600/146 |
| 2014/0142377 A1 * | 5/2014 | Yang | A61B 34/30 |
| | | | 600/104 |
| 2014/0276787 A1 * | 9/2014 | Wang | A61M 25/0147 |
| | | | 606/41 |
| 2014/0276966 A1 * | 9/2014 | Ranucci | A61B 17/068 |
| | | | 606/139 |
| 2015/0112304 A1 | 4/2015 | Silvestro | |
| 2016/0317301 A1 * | 11/2016 | Quadri | A61F 2/2418 |
| 2017/0035567 A1 * | 2/2017 | Duffy | A61F 2/2436 |
| 2017/0215855 A1 * | 8/2017 | Nunan | A61B 17/3421 |
| 2018/0008805 A1 * | 1/2018 | Pleijers | A61B 1/0057 |
| 2018/0028177 A1 | 2/2018 | Van Oepen et al. | |
| 2018/0126119 A1 * | 5/2018 | McNiven | A61M 25/0136 |
| 2019/0030324 A1 * | 1/2019 | Grace | A61N 1/0573 |
| 2019/0110782 A1 * | 4/2019 | Tasci | A61B 17/29 |
| 2019/0133705 A1 * | 5/2019 | Riojas | A61B 34/30 |
| 2019/0231169 A1 * | 8/2019 | Thissen | A61B 1/0055 |
| 2019/0255290 A1 * | 8/2019 | Snyder | A61M 25/0054 |
| 2020/0121166 A1 * | 4/2020 | Thissen | A61B 1/0057 |
| 2020/0163768 A1 * | 5/2020 | Apkarian | A61F 2/243 |
| 2020/0237189 A1 * | 7/2020 | Do | A61B 1/0011 |
| 2021/0022859 A1 | 1/2021 | Crosbie et al. | |
| 2021/0251757 A1 * | 8/2021 | Siegel | A61F 2/2466 |
| 2021/0361428 A1 * | 11/2021 | Dixon | A61F 2/2466 |
| 2022/0151782 A1 * | 5/2022 | Cooper | A61F 2/2436 |
| 2022/0168008 A1 * | 6/2022 | Thissen | A61M 25/0136 |
| 2022/0288356 A1 * | 9/2022 | Hiorth | A61M 25/0138 |
| 2023/0000624 A1 * | 1/2023 | Okabe | A61F 2/2436 |
| 2023/0082226 A1 * | 3/2023 | Lippert | A61M 25/09 |
| | | | 604/164.13 |
| 2023/0364387 A1 * | 11/2023 | Monteon | A61M 25/0147 |
| 2024/0091508 A1 * | 3/2024 | Sharma | A61M 25/09 |
| 2024/0148500 A1 * | 5/2024 | Lopez | A61M 25/0138 |
| 2024/0325146 A1 * | 10/2024 | Von Oepen | A61F 2/2436 |
| 2024/0389835 A1 * | 11/2024 | Thissen | A61B 17/00234 |
| 2024/0407772 A1 * | 12/2024 | Gafford | A61M 25/0138 |
| 2025/0000647 A1 * | 1/2025 | Boyd | A61F 2/2457 |
| 2025/0000650 A1 * | 1/2025 | Ben-Hamou | A61F 2/2436 |
| 2025/0090321 A1 * | 3/2025 | Griswold | A61F 2/2436 |
| 2025/0099243 A1 * | 3/2025 | Haines | A61F 2/2436 |
| 2025/0152353 A1 * | 5/2025 | Fallon | A61F 2/2436 |

FOREIGN PATENT DOCUMENTS

| | | | | |
|---|---|---|---|---|
| WO | 2014144937 A1 | 9/2014 | | |
| WO | WO-2017213491 A1 * | 12/2017 | .......... | A61B 1/0057 |
| WO | WO-2021021368 A1 * | 2/2021 | .......... | A61F 2/2436 |
| WO | 2021080782 A1 | 4/2021 | | |

\* cited by examiner

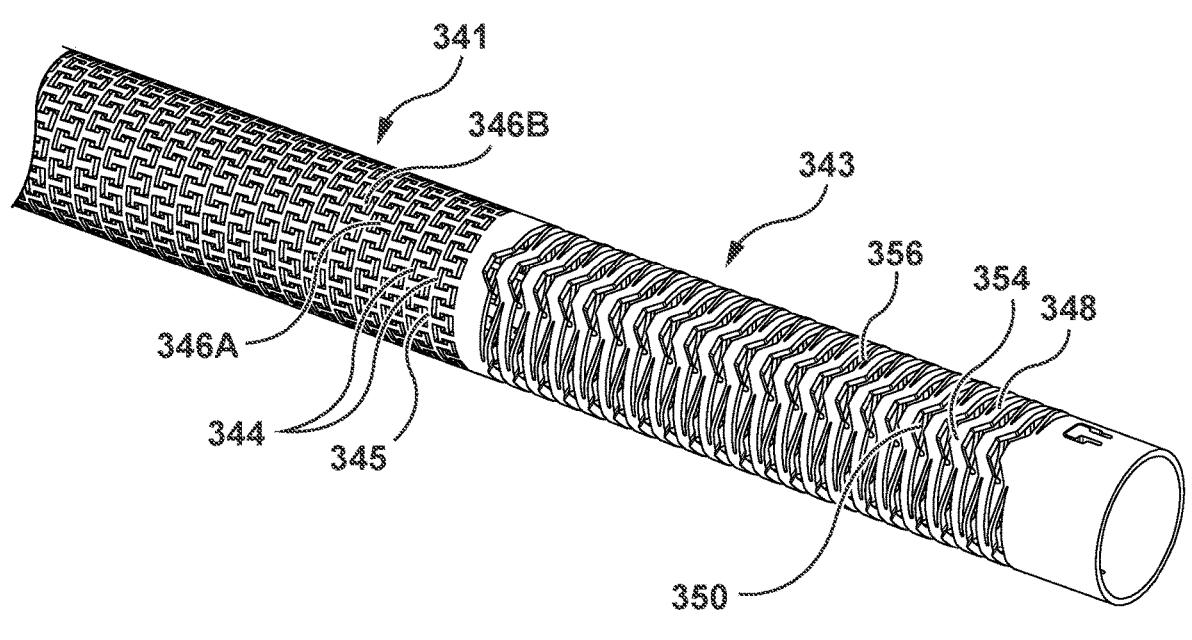
FIG. 9
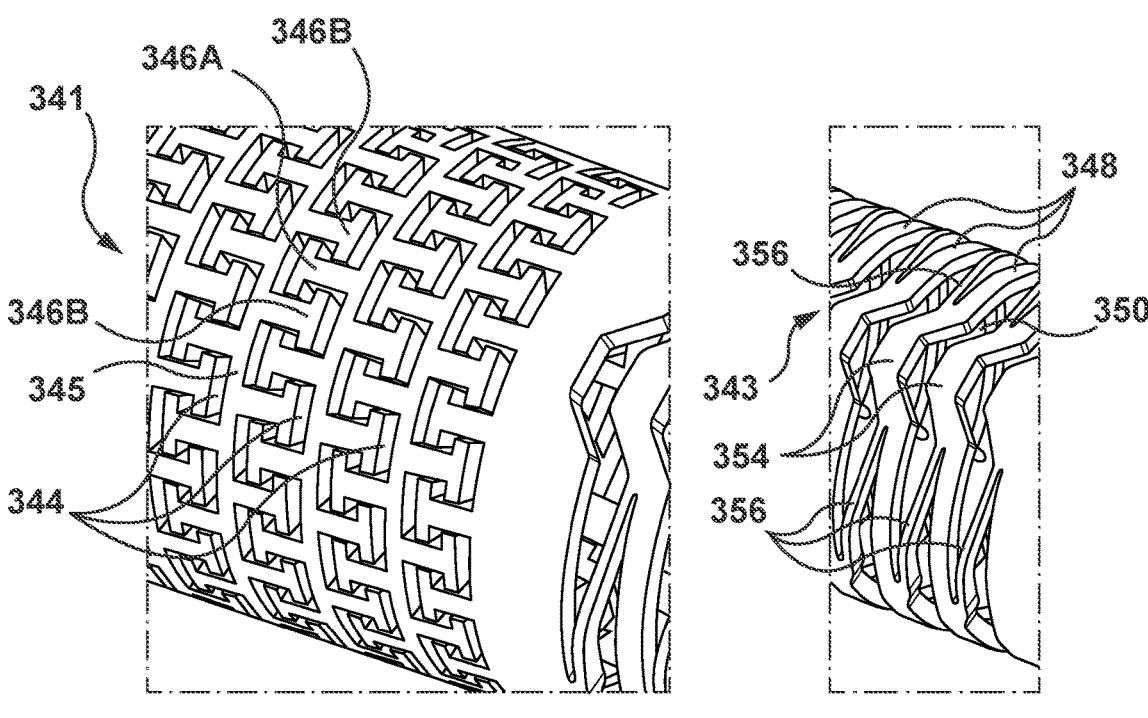
FIG. 10                    FIG. 11

318    370/369    376    104    312

318    370/369    340/341    342/343    316/330    336    104    312

318    370/369    340/341    342/343    316/330    314    104    312

316/330     370/369     318
342/343
312
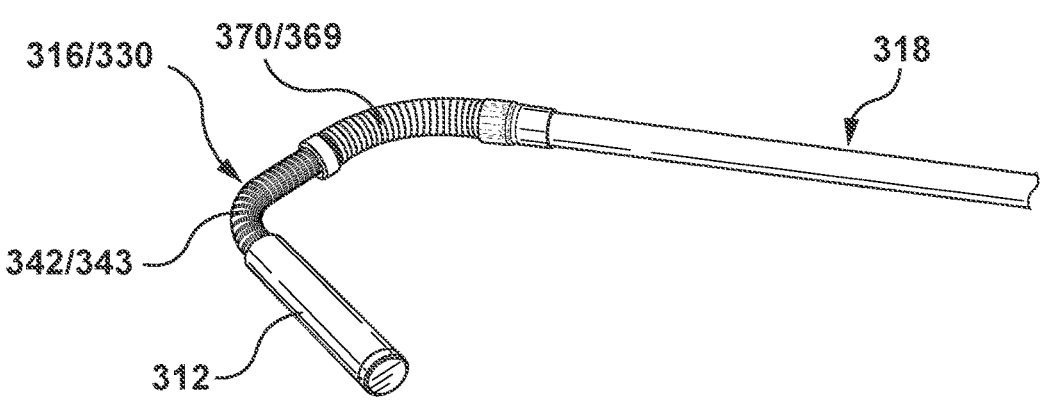
FIG. 23A
312
316/330     318
342/343     370/369
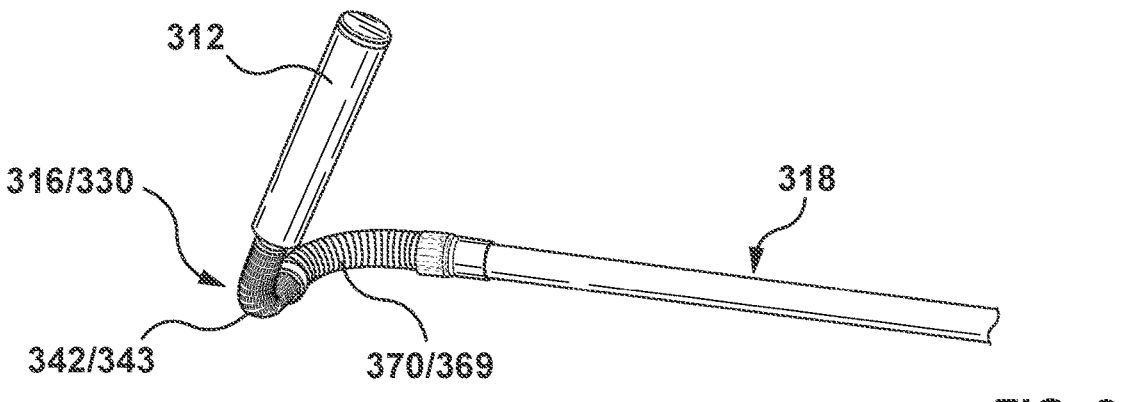
FIG. 23B
312
314
316/330
318
342/343     370/369
FIG. 23C

316/330

320C

104/100

318/370

LA

312

MV

LV

316/330

LA

318/370

314

320A

320B

320C

104

102

312

LV

TRANSCATHETER VALVE DELIVERY SYSTEM WITH OMNIDIRECTIONAL STEERING AND METHODS OF USE THEREOF

CROSS-REFERENCE TO RELATED APPLICATIONS

This application claims the benefit of U.S. Provisional Patent Application Ser. No. 63/222,571, filed Jul. 16, 2021, and U.S. Provisional Patent Application Ser. No. 63/222,583, filed Jul. 16, 2021, each of which is hereby incorporated by reference in its entirety for all purposes.

FIELD OF THE INVENTION

The present invention is related to systems and methods for transcatheter valve delivery and deployment.

BACKGROUND

Heart valve prostheses have been developed for repair and replacement of diseased and/or damaged heart valves. Such heart valve prostheses can be percutaneously delivered and deployed at the site of the diseased heart valve through catheter-based delivery systems. The prosthetic heart valve is loaded onto a delivery system that is able to access and navigate the vasculature to the intended implant location and implant the prosthetic heart valve. A conventional approach for a transcatheter valve system is to use a prosthetic heart valve including a self-expanding stent. Such heart valve prostheses can be delivered while in a low-profile or compressed/contracted configuration so that the valve prosthesis can be advanced through the patient's vasculature. Once positioned at the treatment site, the valve prosthesis can be expanded to engage tissue at the diseased heart valve region to, for instance, hold the valve prosthesis in position. After reaching the delivery site, a capsule constraining the prosthetic heart valve is removed and the prosthetic heart valve is released and expands for deployment. After deployment, the capsule is recovered and the catheter is removed from the patient.

While these valve prostheses offer minimally invasive methods for heart valve repair and/or replacement, challenges remain to providing effective, less invasive, smaller crossing profile prosthetic delivery systems, particularly for mitral valve replacement. For example, catheter delivery approaches and techniques for mitral valve replacement may utilized a transseptal approach. However, with the valve prosthesis retained within a capsule of the delivery system, challenges such as capsule travel within the confined space of the left atrium may limit positioning of a prosthetic heart valve in the native mitral valve. Moreover, the capsule adds to the crossing profile of the catheter. Catheter crossing profile, especially for inter-atrial septum puncture, limit both the feasibility of heart valve prosthetic delivery as well as the size of the prosthetic heart valve.

A delivery system desirably will have a low profile/small outer diameter to facilitate navigation through tortuous vasculature; however, small outer diameter catheters present various design difficulties resulting from competing considerations, resulting in design trade-offs. For instance, such delivery systems must be flexible enough to navigate the tortuous vasculature or anatomy of a patient. However, typical constructions of delivery systems must attempt to balance a requisite flexibility, with axial strength/stiffness (the property that permits the delivery catheter to be pushed and pulled), and torsional strength/stiffness (the property that permits the delivery catheter to be rotated about its longitudinal axis). It is especially important to balance these properties in a distal portion of the delivery system within which a valve prosthesis is held in its compressed, delivery state.

In addition, during delivery and deployment of a prosthetic heart valve, it may become necessary to recover a partially deployed valve. The prosthetic heart valve may be recovered in order to be repositioned, or removal of the prosthetic heart valve may be required may if there is failure during valve delivery. Prosthetic heart valve delivery failure may occur, for example, if the prosthetic heart valve is damaged during deployment. Recovery of the partially deployed prosthetic heart valve may be facilitated by retracting the prosthetic heart valve back into the capsule in which it was delivered. In some cases, it may not be possible to return the entirety of the prosthetic heart valve into the capsule. Any portions protruding from the capsule may create a difficulties in removal of the prosthetic heart valve.

Embodiments hereof are directed to delivery systems for heart valve replacement devices that addresses some of the challenges described above.

SUMMARY

According to a first embodiment hereof, the present disclosure provides a delivery system for deploying a self-expanding prosthetic heart valve. The delivery system includes a flexible shaft, a distal sheath capsule, an inner steerable catheter and an outer steerable catheter. The distal sheath capsule is configured to contain the self-expanding prosthetic heart valve and is disposed over a distal portion of the flexible shaft. The steerable catheter is disposed over the flexible shaft. The inner steerable catheter includes a shaft and an inner distal flex component extending from a distal end of the shaft. The inner distal flex component includes a first cut pattern and a second cut pattern distal to the first cut pattern, the second cut pattern being different from the first cut pattern. The inner steerable catheter is configured to transition between a flexed configuration in which the inner distal flex component is curved along the second cut pattern and a non-flexed configuration in which the inner distal flex component is not curved along the second cut pattern. The outer steerable catheter is slidingly disposed over the inner steerable catheter. The outer steerable catheter includes a shaft and an outer distal flex component extending from a distal end of the shaft. The outer distal flex component includes a third cut pattern. The outer steerable catheter is configured to transition between a flexed configuration in which the outer distal flex component is curved along the third cut pattern and a non-flexed configuration in which the outer distal flex component is not curved along the third cut pattern. Transitioning the inner steerable catheter between the flexed and non-flexed configurations is independent from transitioning the outer steerable catheter between the flexed and non-flexed configurations. The inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

In an aspect of the first embodiment, and in combination with any other aspects herein, the disclosure provides that the second cut pattern of the inner distal flex component is substantially similar to the third cut pattern to the outer distal flex component.

In an aspect of the first embodiment, and in combination with any other aspects herein, the disclosure provides that each of the inner distal flex component and the outer distal flex component is a metallic material.

In an aspect of the first embodiment, and in combination with any other aspects herein, the disclosure provides that the first cut pattern includes a plurality of generally circumferentially extending ribs separated by at least one circumferentially extending slot having a non-linear path that results in each rib of the plurality of ribs including a plurality of alternating T-shaped protrusions.

In an aspect of the first embodiment, and in combination with any other aspects herein, the disclosure further provides a first pullwire extending from a first actuation mechanism of a handle of the inner steerable catheter to a distal end of the inner distal flex component. The first pullwire extends within an annular space between an inner surface of the inner steerable catheter and an outer surface of the flexible shaft. Tensioning of the first pullwire transitions the inner steerable catheter between the flexed and non-flexed configurations.

In an aspect of the first embodiment, and in combination with any other aspects herein, the disclosure provides that the first pullwire has a first end, a second end opposing the first end, and a loop therebetween, the first end and the second end each being attached to the first actuation mechanism of the handle.

In an aspect of the first embodiment, and in combination with any other aspects herein, the disclosure provides that coupling between the loop of the first pullwire and the distal end of the inner distal flex component is weld-free.

In an aspect of the first embodiment, and in combination with any other aspects herein, the disclosure provides that the second cut pattern includes a plurality of generally circumferentially extending ribs separated by a plurality of generally circumferentially extending slots, each slots being circumferentially discontinuous such that the second cut pattern establishes a longitudinal spine. Each rib includes a curve formed thereon that extends towards a proximal end of the inner distal flex component and is configured to nest within a curve of a directly adjacent rib to form a plurality of nesting curves, the plurality of circumferentially opposing curves being circumferentially opposed to the spine.

In an aspect of the first embodiment, and in combination with any other aspects herein, the disclosure provides that the second cut pattern further includes a plurality of cross-struts, each cross-strut extending from a curve of a rib to a directly adjacent proximal rib.

In an aspect of the first embodiment, and in combination with any other aspects herein, the disclosure provides the third pattern cut pattern includes a plurality of generally circumferentially extending ribs separated by a plurality of generally circumferentially extending slots, each slots being circumferentially discontinuous such that the third cut pattern establishes a longitudinal spine. Each rib includes a curve formed thereon that extends towards a proximal end of the outer distal flex component and is configured to nest within a curve of a directly adjacent rib to form a plurality of nesting curves, the plurality of circumferentially opposing curves being circumferentially opposed to the spine.

In an aspect of the first embodiment, and in combination with any other aspects herein, the disclosure provides that the third cut pattern further includes a plurality of cross-struts, each cross-strut extending from a curve of a rib to a directly adjacent proximal rib.

In an aspect of the first embodiment, and in combination with any other aspects herein, the disclosure further provides a second pullwire extending from a second actuation mechanism of a handle of the outer steerable catheter to a distal end of the outer distal flex component. The second pullwire extends within an annular space between an inner surface of the outer steerable catheter and an outer surface of the inner steerable catheter. Tensioning of the second pullwire transitions the outer steerable catheter between the flexed and non-flexed configurations.

In an aspect of the first embodiment, and in combination with any other aspects herein, the disclosure provides that the second pullwire has a first end, a second end opposing the first end, and a loop therebetween, the first end and the second end each being attached to the second actuation mechanism of the handle.

In an aspect of the first embodiment, and in combination with any other aspects herein, the disclosure provides that coupling between the loop of the second pullwire and the distal end of the outer distal flex component is weld-free.

In an aspect of the first embodiment, and in combination with any other aspects herein, the disclosure provides that the distal end of the inner distal flex component includes a cap and the loop of the second pullwire is coupled to the cap.

In an aspect of the first embodiment, and in combination with any other aspects herein, the disclosure provides that the inner steerable catheter includes at least one lumen formed therein for receiving a suture slidingly disposed therethrough.

In an aspect of the first embodiment, and in combination with any other aspects herein, the disclosure provides that the inner steerable catheter includes a dual lumen tube for receiving a single continuous suture slidingly disposed therethrough.

In an aspect of the first embodiment, and in combination with any other aspects herein, the disclosure provides that the inner steerable catheter is slidingly disposed over the flexible shaft such that the flexible shaft is configured to move axially relative to the inner steerable catheter.

In an aspect of the first embodiment, and in combination with any other aspects herein, the disclosure provides that the inner steerable catheter is rotatable 360 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

According to a second embodiment hereof, the present disclosure provides a delivery system for deploying a self-expanding prosthetic heart valve. The delivery system includes an inner steerable catheter and an outer steerable catheter. The inner steerable catheter includes a shaft and an inner distal flex component extending from a distal end of the shaft. The inner distal flex component includes a first cut pattern and a second cut pattern distal to the first cut pattern, the second cut pattern being different from the first cut pattern. The inner steerable catheter is configured to transition between a flexed configuration in which the inner distal flex component is curved along the second cut pattern and a non-flexed configuration in which the inner distal flex component is not curved along the second cut pattern. The outer steerable catheter is slidingly disposed over the inner steerable catheter. The outer steerable catheter includes a shaft and an outer distal flex component extending from a distal end of the shaft. The outer distal flex component includes a third cut pattern. The outer steerable catheter is configured to transition between a flexed configuration in which the outer distal flex component is curved along the third cut pattern and a non-flexed configuration in which the outer distal flex component is not curved along the third cut pattern. Transitioning the inner steerable catheter between the flexed and non-flexed configurations is independent from transitioning the outer steerable catheter between the flexed and non-flexed configurations. The inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

In an aspect of the second embodiment, and in combination with any other aspects herein, the disclosure provides that the second cut pattern of the inner distal flex component is substantially similar to the third cut pattern to the outer distal flex component.

In an aspect of the second embodiment, and in combination with any other aspects herein, the disclosure provides that each of the inner distal flex component and the outer distal flex component is a metallic material.

In an aspect of the second embodiment, and in combination with any other aspects herein, the disclosure provides that the first cut pattern includes a plurality of generally circumferentially extending ribs separated by at least one circumferentially extending slot having a non-linear path that results in each rib of the plurality of ribs including a plurality of alternating T-shaped protrusions.

In an aspect of the second embodiment, and in combination with any other aspects herein, the disclosure further provides a first pullwire extending from a first actuation mechanism of a handle of the inner steerable catheter to a distal end of the inner distal flex component. The first pullwire extending within an annular space between an inner surface of the inner steerable catheter and an outer surface of the flexible shaft. Tensioning of the first pullwire transitions the inner steerable catheter between the flexed and non-flexed configurations.

In an aspect of the second embodiment, and in combination with any other aspects herein, the disclosure provides that the first pullwire has a first end, a second end opposing the first end, and a loop therebetween, the first end and the second end each being attached to the first actuation mechanism of the handle.

In an aspect of the second embodiment, and in combination with any other aspects herein, the disclosure provides that coupling between the loop of the first pullwire and the distal end of the inner distal flex component is weld-free.

In an aspect of the second embodiment, and in combination with any other aspects herein, the disclosure provides that the second cut pattern includes a plurality of generally circumferentially extending ribs separated by a plurality of generally circumferentially extending slots, each slots being circumferentially discontinuous such that the second cut pattern establishes a longitudinal spine. Each rib includes a curve formed thereon that extends towards a proximal end of the inner distal flex component and is configured to nest within a curve of a directly adjacent rib to form a plurality of nesting curves, the plurality of circumferentially opposing curves being circumferentially opposed to the spine.

In an aspect of the second embodiment, and in combination with any other aspects herein, the disclosure provides that the second cut pattern further includes a plurality of cross-struts, each cross-strut extending from a curve of a rib to a directly adjacent proximal rib.

In an aspect of the second embodiment, and in combination with any other aspects herein, the disclosure provides that the third pattern cut pattern includes a plurality of generally circumferentially extending ribs separated by a plurality of generally circumferentially extending slots, each slots being circumferentially discontinuous such that the third cut pattern establishes a longitudinal spine. Each rib includes a curve formed thereon that extends towards a proximal end of the outer distal flex component and is configured to nest within a curve of a directly adjacent rib to form a plurality of nesting curves, the plurality of circumferentially opposing curves being circumferentially opposed to the spine.

In an aspect of the second embodiment, and in combination with any other aspects herein, the disclosure provides that third cut pattern further includes a plurality of cross-struts, each cross-strut extending from a curve of a rib to a directly adjacent proximal rib.

In an aspect of the second embodiment, and in combination with any other aspects herein, the disclosure further provides a second pullwire extending from a second actuation mechanism of a handle of the outer steerable catheter to a distal end of the outer distal flex component. The second pullwire extends within an annular space between an inner surface of the outer steerable catheter and an outer surface of the inner steerable catheter. Tensioning of the second pullwire transitions the outer steerable catheter between the flexed and non-flexed configurations.

In an aspect of the second embodiment, and in combination with any other aspects herein, the disclosure provides that the second pullwire has a first end, a second end opposing the first end, and a loop therebetween, the first end and the second end each being attached to the second actuation mechanism of the handle.

In an aspect of the second embodiment, and in combination with any other aspects herein, the disclosure provides that coupling between the loop of the second pullwire and the distal end of the outer distal flex component is weld-free.

In an aspect of the second embodiment, and in combination with any other aspects herein, the disclosure provides that the inner steerable catheter is rotatable 360 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

According to a third embodiment hereof, the present disclosure provides a steerable catheter comprising a flexible shaft, and a flexible component disposed over the flexible shaft. The flexible component has a first longitudinal portion and a second longitudinal portion that is distal to the first longitudinal portion. The first longitudinal portion has a free state in which it is floppy and a second state in which it is self-standing. The first longitudinal portion is self-standing when sufficiently compressed in a longitudinal direction.

In an aspect of the third embodiment, and in combination with any other aspects herein, the disclosure provides that the first longitudinal portion is self-standing when compressed to have sufficient column strength.

In an aspect of the third embodiment, and in combination with any other aspects herein, the disclosure provides that the first longitudinal portion column strength can transition between different values depending upon the compressive force placed on it in the longitudinal direction.

In an aspect of the third embodiment, and in combination with any other aspects herein, the disclosure provides that when the first longitudinal portion is in its free state, it has insufficient column strength to be self-standing.

In an aspect of the third embodiment, and in combination with any other aspects herein, the disclosure provides that when the first longitudinal portion is in its free state, it has insufficient column strength to maintain axial alignment along its length.

In an aspect of the third embodiment, and in combination with any other aspects herein, the disclosure provides that the steerable catheter has a proximal portion and a distal portion, and further includes a pullwire. The pullwire is connected to the proximal and distal portions.

In an aspect of the third embodiment, and in combination with any other aspects herein, the disclosure provides that a channel is formed between the flexible shaft and the flexible component. The pullwire is arranged in the channel such that a portion of the pullwire can freely move in a circumferential direction.

In an aspect of the third embodiment, and in combination with any other aspects herein, the disclosure provides that the pullwire is arranged in the channel such that it can freely move in a circumferential direction along the first and second longitudinal portions.

In an aspect of the third embodiment, and in combination with any other aspects herein, the disclosure provides that a portion of the pullwire is free to move 360 degrees.

In an aspect of the third embodiment, and in combination with any other aspects herein, the disclosure provides that the channel is annular.

In an aspect of the third embodiment, and in combination with any other aspects herein, the disclosure provides that the when the pullwire is tensioned, a compressive force is placed on the first longitudinal portion.

In an aspect of the third embodiment, and in combination with any other aspects herein, the disclosure provides that the when the pullwire is sufficiently tensioned, the second longitudinal portion bends.

In an aspect of the third embodiment, and in combination with any other aspects herein, the disclosure provides that the when the pullwire is sufficiently tensioned, the first longitudinal portion has sufficient column strength to be self-standing and the second longitudinal portion has a curved configuration.

In an aspect of the third embodiment, and in combination with any other aspects herein, the disclosure provides that the second longitudinal portion can be curved 90 degrees.

In an aspect of the third embodiment, and in combination with any other aspects herein, the disclosure provides that the second longitudinal portion can be curved 360 degrees.

In an aspect of the third embodiment, and in combination with any other aspects herein, the disclosure provides that the curvature of the second longitudinal portion can be changed without substantially changing the shape of the first longitudinal portion.

In an aspect of the third embodiment, and in combination with any other aspects herein, the disclosure provides that the flexible component is slidably disposed over the flexible shaft.

In an aspect of the third embodiment, and in combination with any other aspects herein, the disclosure provides that when the first longitudinal portion is in a self-standing state, a force can be applied on it to bend it and when that force is removed it tends to move toward the self-standing configuration it had before the force was applied.

According to a fourth embodiment hereof, the present disclosure provides a steering apparatus for delivery of a prosthesis. The steering apparatus includes a flexible shaft, a capsule configured to contain the prosthesis and coupled to the flexible shaft, an inner steerable catheter disposed over the flexible shaft, and an outer steerable catheter slidingly disposed over the inner steerable catheter. The inner steerable catheter has a distal portion and includes a shaft and a flexible component in the vicinity of the distal portion. The flexible component includes a first cut pattern and a second cut pattern, the second cut pattern being different from the first cut pattern. The outer steerable catheter has a distal end portion and includes a shaft and a flexible component in the vicinity of the outer steerable catheter portion. The outer steerable catheter flexible component includes a third cut pattern.

In an aspect of the fourth embodiment, and in combination with any other aspects herein, the disclosure provides that transitioning the inner steerable catheter between the flexed and non-flexed configurations is independent from transitioning the outer steerable catheter between the flexed and non-flexed configurations.

In an aspect of the fourth embodiment, and in combination with any other aspects herein, the disclosure provides that the inner steerable catheter is rotatable relative to the outer steerable catheter when the third cut pattern is disposed over at least a portion of the first cut pattern and each of the inner steerable catheter and the outer steerable catheter is in a flexed configuration.

In an aspect of the fourth embodiment, and in combination with any other aspects herein, the disclosure provides that the inner steerable catheter is rotatable at least 90 degrees relative to the outer steerable catheter when the third cut pattern is disposed over at least a portion of the first cut pattern and each of the inner steerable catheter and the outer steerable catheter is in a flexed configuration.

According to a fifth embodiment hereof, the present disclosure provides a delivery system including an inner steerable catheter including a shaft and an inner distal flex component extending from a distal end of the shaft, and an outer steerable catheter slidingly disposed over the inner steerable catheter. The inner distal flex component includes a first cut pattern and a second cut pattern distal to the first cut pattern, the second cut pattern being different from the first cut pattern. The inner steerable catheter is configured to transition between a flexed configuration in which the inner distal flex component is curved along the second cut pattern and a non-flexed configuration in which the inner distal flex component is not curved along the second cut pattern. The outer steerable catheter includes a shaft and an outer distal flex component extending from a distal end of the shaft, wherein the outer distal flex component includes a third cut pattern. The outer steerable catheter is configured to transition between a flexed configuration in which the outer distal flex component is curved along the third cut pattern and a non-flexed configuration in which the outer distal flex component is not curved along the third cut pattern.

In an aspect of the fifth embodiment, and in combination with any other aspects herein, the disclosure provides that transitioning the inner steerable catheter between the flexed and non-flexed configurations is independent from transitioning the outer steerable catheter between the flexed and non-flexed configurations.

In an aspect of the fifth embodiment, and in combination with any other aspects herein, the disclosure provides that the inner steerable catheter is rotatable relative to the outer steerable catheter when the third cut pattern of the outer distal flex component is disposed over at least a portion of the first cut pattern of the inner distal flex component and each of the inner steerable catheter and the outer steerable catheter is in the flexed configuration.

In an aspect of the fifth embodiment, and in combination with any other aspects herein, the disclosure provides that the inner steerable catheter is rotatable relative to the outer steerable catheter when the third cut pattern of the outer distal flex component is disposed over at least a portion of the first cut pattern of the inner distal flex component and each of the inner steerable catheter and the outer steerable catheter is in the flexed configuration.

According to a sixth embodiment hereof, the present disclosure provides a method of loading a suture into a delivery system. A first end of a suture is coupled to a distal end of a first mandrel. The first mandrel is slidingly disposed through a first lumen of a delivery system and a proximal end of the first mandrel extends out of a handle of the delivery system. The suture includes a loop between the first end and a second end thereof and the loop is disposed circumferentially around an inflow edge of a prosthetic heart valve. The second end of the suture is coupled to a distal end of a second mandrel. The second mandrel is slidingly disposed through a second lumen of the delivery system. The second lumen is separate from the first lumen and a proximal end of the second mandrel extends out of the handle of the delivery system. The first mandrel with the first end of the suture coupled thereto is proximally retracted to pull the suture through the first lumen of the delivery system until the first end of the suture extends out of the handle of the delivery system. The second mandrel with the second end of the suture coupled thereto is proximally retracted to pull the suture through the second lumen of the delivery system until the second end of the suture extends out of the handle of the delivery system. The first mandrel is uncoupled from the first end of the suture. The second mandrel is uncoupled from the second end of the suture. The prosthetic heart valve is coupled to the delivery system via the suture which remains loaded into the delivery system with a first leg of the suture extending through the first lumen of the delivery system and a second leg of the suture extending through the second lumen of the delivery system, the loop disposed circumferentially around the inflow edge of the prosthetic heart valve.

In an aspect of the sixth embodiment, and in combination with any other aspects herein, the disclosure provides locking the position of the suture relative to the delivery system after the first mandrel is uncoupled from the first end of the suture and the second mandrel is uncoupled from the second end of the suture.

In an aspect of the sixth embodiment, and in combination with any other aspects herein, the disclosure provides that the first lumen of the delivery system and the second lumen of the delivery system are formed from a dual lumen tube.

In an aspect of the sixth embodiment, and in combination with any other aspects herein, the disclosure provides that the prosthetic heart valve is preloaded with the loop of the suture disposed circumferentially around the inflow edge of the prosthetic heart valve.

In an aspect of the sixth embodiment, and in combination with any other aspects herein, the disclosure provides that a suture length except for the loop of the suture is wrapped around a spool.

In an aspect of the sixth embodiment, and in combination with any other aspects herein, the disclosure provides that during the steps of proximally retracting the first mandrel and proximally retracting the second mandrel, the suture length is unwrapped from the spool.

In an aspect of the sixth embodiment, and in combination with any other aspects herein, the disclosure provides that the loop of the suture is disposed within an integral folded pocket of a graft material of the prosthetic heart valve.

In an aspect of the sixth embodiment, and in combination with any other aspects herein, the disclosure provides the loop of the suture extends circumferentially between 350 degrees and 359 degrees around the inflow edge of the prosthetic heart valve.

In an aspect of the sixth embodiment, and in combination with any other aspects herein, the disclosure provides that the delivery system is preloaded with the first mandrel disposed through the first lumen of the delivery system and the second mandrel disposed through the second lumen of the delivery system.

In an aspect of the sixth embodiment, and in combination with any other aspects herein, the disclosure provides that the distal end of the first mandrel includes a first hook and the step of coupling the first end of the suture to the distal end of the first mandrel including positioning the first end of the suture into the first hook. The distal end of the second mandrel includes a second hook and the step of coupling the second end of the suture to the distal end of the second mandrel including positioning the second end of the suture into the second hook.

According to a seventh embodiment hereof, the present disclosure provides a method of loading a suture into a delivery system. A prosthetic heart valve is positioned proximate to a delivery system. The prosthetic heart valve is preloaded with a suture including a loop between a first end and a second end thereof, the loop of the suture being disposed circumferentially around the inflow edge of the prosthetic heart valve. The delivery system is preloaded with a first mandrel slidingly disposed through a first lumen of the delivery system and a second mandrel slidingly disposed through a second lumen of the delivery system. The first end of the suture is coupled to a distal end of the first mandrel. The second end of the suture is coupled to a distal end of a second mandrel. The first mandrel with the first end of the suture coupled thereto is proximally retracted to pull the suture through the first lumen of the delivery system until the first end of the suture extends out of a handle of the delivery system. The second mandrel with the second end of the suture coupled thereto is proximally retracted to pull the suture through the second lumen of the delivery system until the second end of the suture extends out of the handle of the delivery system. The first mandrel is uncoupled from the first end of the suture. The second mandrel is uncoupled from the second end of the suture. The prosthetic heart valve is coupled to the delivery system via the suture which remains loaded into the delivery system with a first leg of the suture extending through the first lumen of the delivery system and a second leg of the suture extending through the second lumen of the delivery system, the loop disposed circumferentially around the inflow edge of the prosthetic heart valve.

In an aspect of the seventh embodiment, and in combination with any other aspects herein, the disclosure provides locking the position of the suture relative to the delivery system after the first mandrel is uncoupled from the first end of the suture and the second mandrel is uncoupled from the second end of the suture.

In an aspect of the seventh embodiment, and in combination with any other aspects herein, the disclosure provides that the first lumen of the delivery system and the second lumen of the delivery system are formed from a dual lumen tube.

In an aspect of the seventh embodiment, and in combination with any other aspects herein, the disclosure provides that the prosthetic heart valve is preloaded with a suture length except for the loop of the suture being wrapped around a spool.

In an aspect of the seventh embodiment, and in combination with any other aspects herein, the disclosure provides that during the steps of proximally retracting the first mandrel and proximally retracting the second mandrel, the suture length is unwrapped from the spool.

In an aspect of the seventh embodiment, and in combination with any other aspects herein, the disclosure provides that the loop of the suture is disposed within an integral folded pocket of a graft material of the prosthetic heart valve.

In an aspect of the seventh embodiment, and in combination with any other aspects herein, the disclosure provides that the loop of the suture extends circumferentially between 350 degrees and 359 degrees around the inflow edge of the prosthetic heart valve.

In an aspect of the seventh embodiment, and in combination with any other aspects herein, the disclosure provides that the distal end of the first mandrel includes a first hook and the step of coupling the first end of the suture to the distal end of the first mandrel including positioning the first end of the suture into the first hook, and wherein the distal end of the second mandrel includes a second hook and the step of coupling the second end of the suture to the distal end of the second mandrel including positioning the second end of the suture into the second hook.

BRIEF DESCRIPTION OF THE DRAWINGS

The accompanying figures, which are incorporated herein, form part of the specification and illustrate embodiments of a prosthesis delivery system. Together with the description, the figures further explain the principles of and enable a person skilled in the relevant art(s) to make and use the delivery catheters described herein. The drawings are provided to illustrate various features of the embodiments described herein and are not necessarily drawn to scale. In the drawings, like reference numbers indicate identical or functionally similar elements.

FIG. 9 is a perspective view of an inner distal flex component of the inner steerable catheter of FIG. 6, wherein the inner distal flex component is removed from the inner steerable catheter for sake of illustration.

FIG. 10 is an enlarged view of a first cut pattern of a first longitudinal portion of the inner distal flex component of FIG. 9.

FIG. 11 is an enlarged view of a second cut pattern of a second longitudinal portion of the inner distal flex component of FIG. 9.

FIGS. 23A-23C illustrate relative axial and rotational movement between the inner steerable catheter and the outer steerable catheter, with each of the inner steerable catheter and the outer steerable catheter being in the flexed configuration.

DETAILED DESCRIPTION OF THE INVENTION

Specific embodiments of the present invention are now described with reference to the figures. Unless otherwise indicated, for the delivery catheters discussed herein, the terms "distal" and "proximal" are used in the following description with respect to a position or direction relative to the treating clinician or operator. "Distal" and "distally" are positions distant from or in a direction away from the clinician, and "proximal" and "proximally" are positions near or in a direction toward the clinician.

The following detailed description is merely illustrative in nature and is not intended to limit the invention or the application and uses of the invention. Although the description of the invention is in the context of catheter enabled delivery and deployment of prosthetic heart valves, aspects of the invention may also be used in any other context that is useful. As an example, the description of the invention is in the context of delivery and deployment of heart valve prostheses. Prosthesis or prostheses may include any prosthesis including an expandable structure. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background summary or the following detailed description.

Embodiments hereof are related to a delivery system with omnidirectional steering suitable for intravascular delivery of a prosthetic heart valve to a native valve in a heart of a patient. In some embodiments, delivery catheters and methods are presented for the treatment of valve disease as part of procedure steps for minimally invasive implantation of an artificial or prosthetic heart valve, such as a mitral valve. For example, a heart delivery system, in accordance with embodiments described herein, can be used to percutaneously direct and deliver a mitral valve prosthesis via an intravascular retrograde approach across an aortic valve, into a left ventricle and across a diseased or damaged mitral valve in a patient, such as in a patient suffering from mitral valve prolapse. In another embodiment, a heart delivery system, in accordance with embodiments described herein, can be used to direct and deliver an aortic valve prosthesis via an aortic approach across an aortic arch, into an aortic sinus and across a diseased or damaged aortic valve in a patient. In further embodiments, the delivery systems and delivery catheters disclosed herein are suitable for prosthetic heart valve delivery across other diseased or damaged natural heart valves or prior implanted prosthetic heart valves, such as tricuspid, and pulmonary heart valves.

Figures 1, 2:
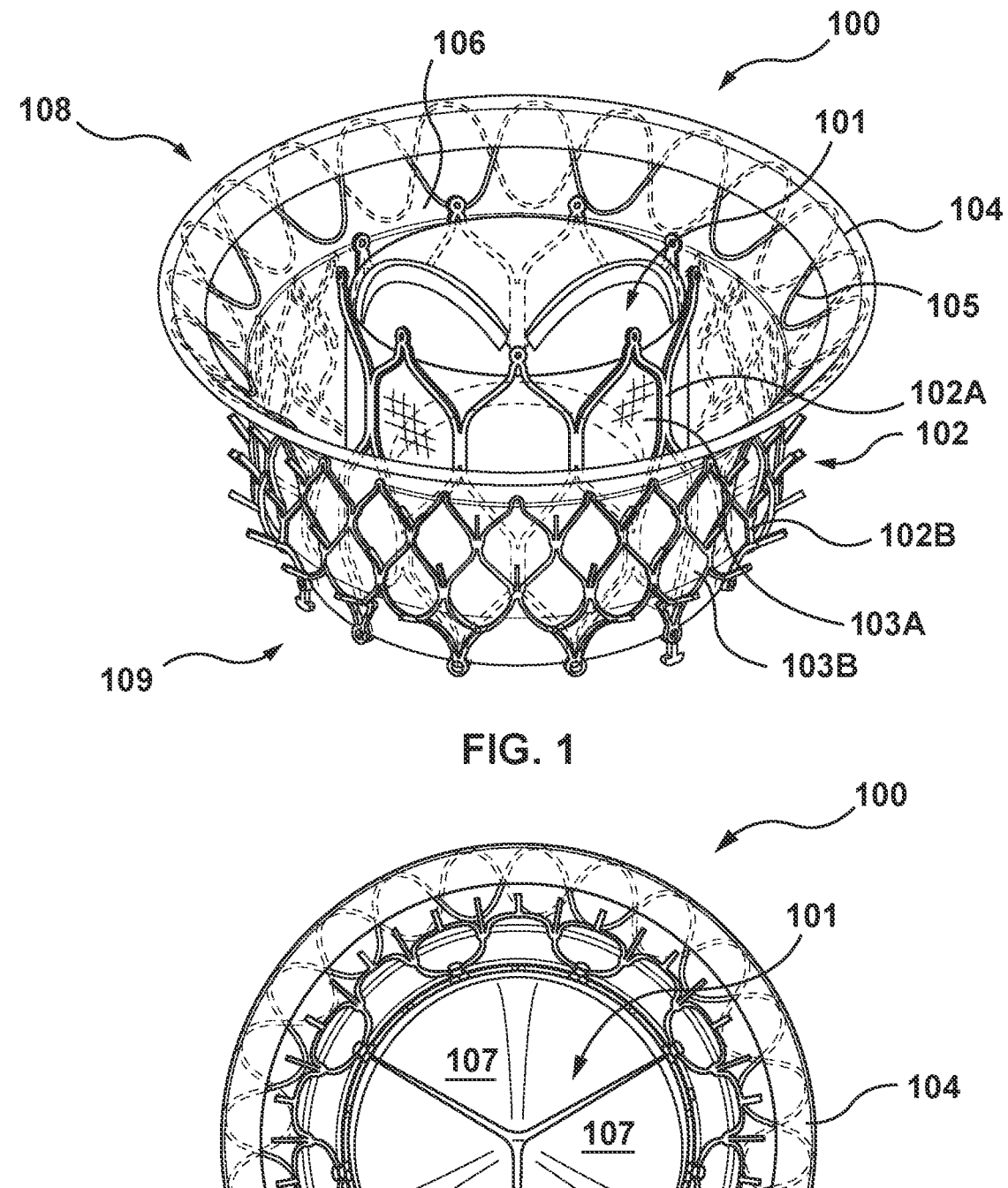
FIG. 1 depicts a perspective view of a prosthetic heart valve in accordance with an aspect of the disclosure.
FIG. 2 depicts an atrial end view of the prosthetic heart valve shown in FIG. 1.

Embodiments hereof relate to a delivery system with omnidirectional steering for delivering a prosthetic heart valve 100. FIGS. 1 and 2 illustrate an exemplary prosthetic heart valve 100 for use in embodiments hereof, wherein the prosthetic heart valve 100 is in an expanded or deployed configuration in accordance with an embodiment hereof. Prosthetic heart valve 100 is illustrated herein in order to facilitate description of delivery catheters and systems to be utilized in conjunction therewith according to embodiments hereof. It is understood that any number of alternate heart valve prostheses can be used with the methods and devices described herein. The prosthetic heart valve 100 is presented by way of example only, and other shapes and designs of prosthetic heart valves are also consistent with embodiments hereof. Other non-limiting examples of prosthetic heart valves that can be delivered via the delivery systems and methods described herein are described in U.S. application Ser. No. 16/853,851 to McVeigh et al., U.S. Pat. No. 9,034,032 to McLean et al. and International Patent Application No. PCT/US5114/029549 to McLean et al, U.S. Patent Application Publication No. 5112/0101572 to Kovalsky et al., U.S. Patent Application Publication No. 5112/ 0035722 to Tuval, U.S. Patent Application Publication No. 2006/0265056 to Nguyen et al., U.S. Patent Application Publication No. 2007/05409266 to Birdsall, and U.S. Patent Application Publication No. 2007/05409269 to Dolan et al., each of which is incorporated by reference herein in its entirety. Although the prosthetic heart valve 100 is configured for placement within a mitral heart valve, embodiments of delivery systems and techniques described herein may be used in conjunction with any transcatheter valve prostheses. For example, embodiments described herein may be utilized with a transcatheter prosthetic heart valve configured for placement within a pulmonary, aortic, mitral, or tricuspid valve, or may be utilized with a transcatheter valve prosthesis configured for placement within a venous valve or within other body passageways where it is deemed useful. There is no intention to be bound by any expressed or implied theory presented in the preceding technical field, background, brief summary or the following detailed description.

The prosthetic heart valve 100 is configured to be radially compressed into a reduced-diameter configuration (not shown) for delivery within a vasculature and to return to an expanded, deployed configuration, which is shown in FIGS. 1 and 2. In accordance with embodiments hereof, when in the radially compressed or reduced-diameter configuration, the prosthetic heart valve 100 has a low profile suitable for delivery to and deployment within a native heart valve via a suitable delivery system that may be tracked to the deployment site of the native heart valve of a heart via any one of a transseptal, retrograde, or transapical approach. The prosthetic heart valve 100 includes a stent or frame 102 and a prosthetic valve component 101 including at least one leaflet 107 disposed within and secured to the frame 102. The prosthetic valve component 101 of the transcatheter heart valve prosthesis 100 is capable of regulating flow therethrough via valve leaflets that may form a replacement valve.

Any portion of the frame 102 described herein as an element of a heart valve prothesis 100 may be made from any number of suitable biocompatible materials, e.g., stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material would be selected to provide the transcatheter heart valve prothesis 100 to be configured to be compressed into a reduced-diameter crimped configuration for transcatheter delivery to a native valve, whereby release from a delivery catheter returns the prosthesis to an expanded, deployed configuration. Alternatively, the prosthetic heart valve 100 may be balloon-expandable as would be understood by one of ordinary skill in the art.

In an aspect of the disclosure, the frame 102 of the transcatheter heart valve prosthesis 100 includes a valve support 102A at least partially surrounded by and coupled to an anchor element 102B. The valve support 102A is a tubular stent-like or frame structure that defines a central lumen from a first end 108 of the valve support 102A to a second end 109 of the valve support 102A. When positioned in situ within a native mitral valve, the first end 108 is an inflow or upstream end and the second end 109 is an outflow or downstream end. The valve support 102A is configured to support the prosthetic valve component 101 therein. The anchor element 102B of the frame 102 functions as an anchor for the transcatheter heart valve prosthesis 100 to secure its deployed position within a native annulus. The anchor element 102B is a substantially cylindrically-shaped structure that is configured to engage heart tissue at or below an annulus of a native heart valve, such as an annulus of a native mitral valve.

Each of the valve support 102A and the anchor 102B include a skirt or graft material 103A, 103B, respectively, secured thereto. More particularly, the graft material 103A is coupled to an inner surface of the valve support 102A to line a portion thereof. Alternatively, the graft material 103A may be coupled to an outer surface of the valve support 102A to enclose a portion thereof as would be known to one of ordinary skill in the art of prosthetic valve construction. The graft material 103A, 103B may be a natural or biological material such as pericardium or another membranous tissue such as intestinal submucosa. Alternatively, the graft material 103A, 103B may be a low-porosity woven fabric, such as polyester, Dacron fabric, or PTFE, which creates a one-way fluid passage when attached to the stent.

The prosthetic heart valve 100 further includes a valve brim 104 that extends outwardly from an upstream end of the anchor element 102B. The valve brim 104 is formed by a brim support 105 and a portion of graft material 103B that extends past or beyond the inflow end of the anchor 102B. More particularly, the graft material 103B is coupled to an inner surface of the anchor element 102B to line a portion thereof. The graft material 103B extends past or beyond the inflow end of the anchor element 102B, and includes an integral folded pocket or hem beyond the inflow end of the anchor element 102B. The brim support 105 is disposed within this folded pocket of the graft material 103B. The brim support 105 includes overlapping, 180 degree out of phase sinusoidal wire forms. The valve brim 104 may act as an atrial retainer, if present, and to serve such a function the valve brim 104 may be configured to engage tissue above a native annulus, such as a supra-annular surface or some other tissue in the left atrium, to thereby inhibit downstream migration of a prosthetic heart valve 100, for e.g., during atrial systole. Accordingly, the valve brim 104 is of a larger diameter than the frame 102 and extends radially outward from the anchor element 102B. The portion of graft material 103B connecting the valve brim 104 to the anchor element 102B is referred to herein as a valve brim hinge 106. The valve brim hinge 106 is configured to permit the valve brim 104 to hinge and/or flex with respect to the remainder of the prosthetic heart valve 100.

Figure 3:
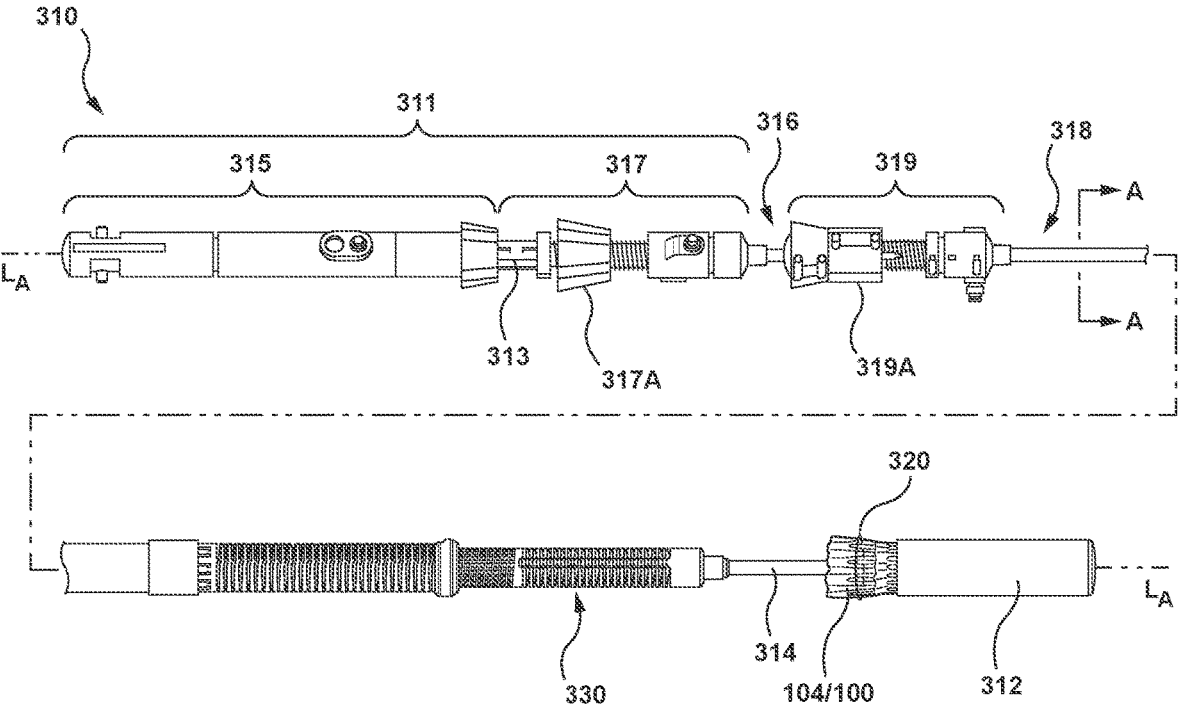
FIG. 3 depicts a side view of a delivery system according to an embodiment hereof, wherein the prosthetic heart valve of FIG. 1 is loaded into a distal sheath capsule of the delivery system.
Figure 3A:
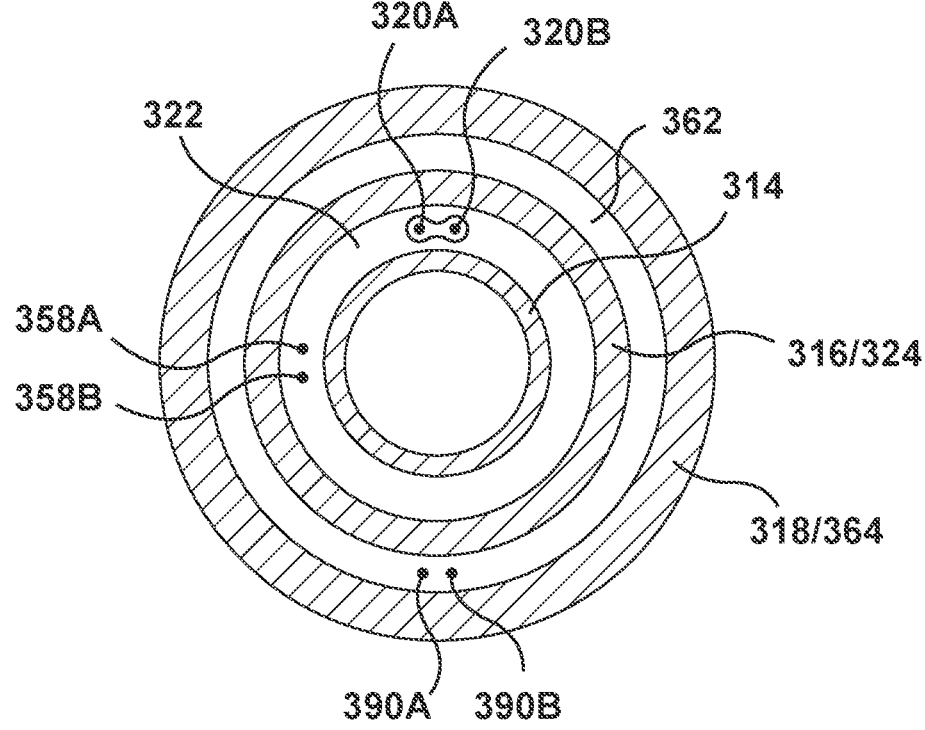
FIG. 3A is a cross-sectional view taken along line A-A of FIG. 3.
Figure 4:
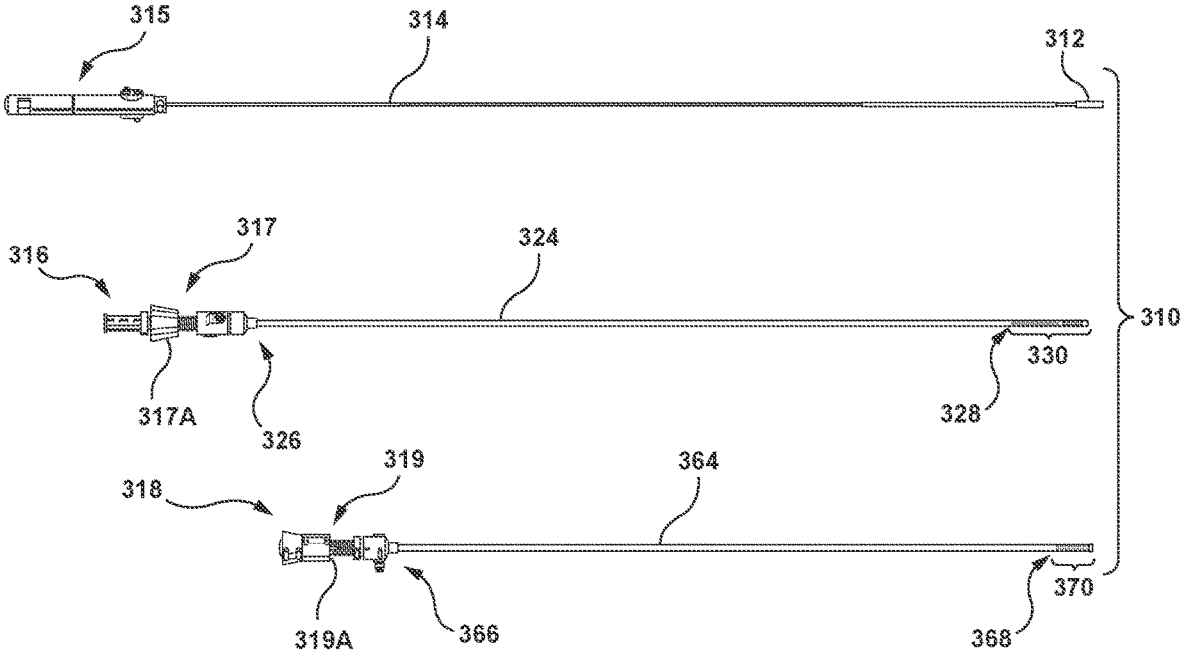
FIG. 4 is an exploded view of the delivery system of FIG. 3.
Figure 5:
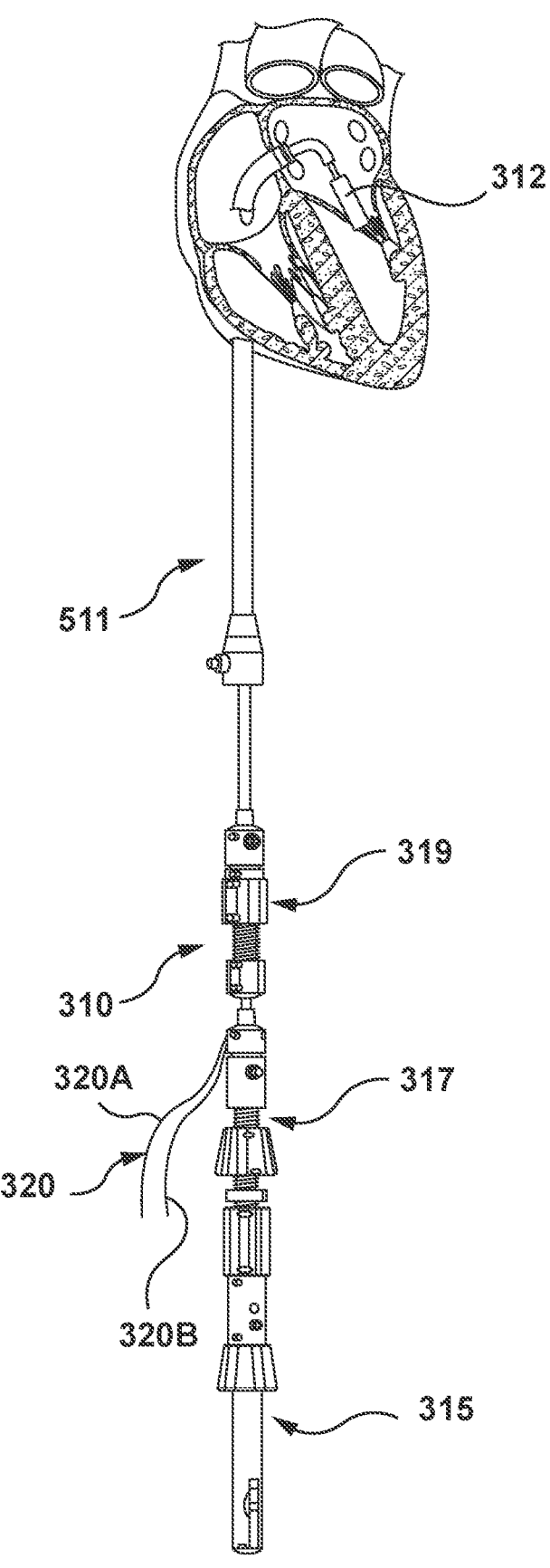
FIG. 5 is a schematic illustration of the delivery system of FIG. 3 being utilized to deliver a prosthetic heart valve to a native mitral valve according to an embodiment hereof, wherein the delivery system is delivered through an introducer sheath.
Figures 6, 7, 8:
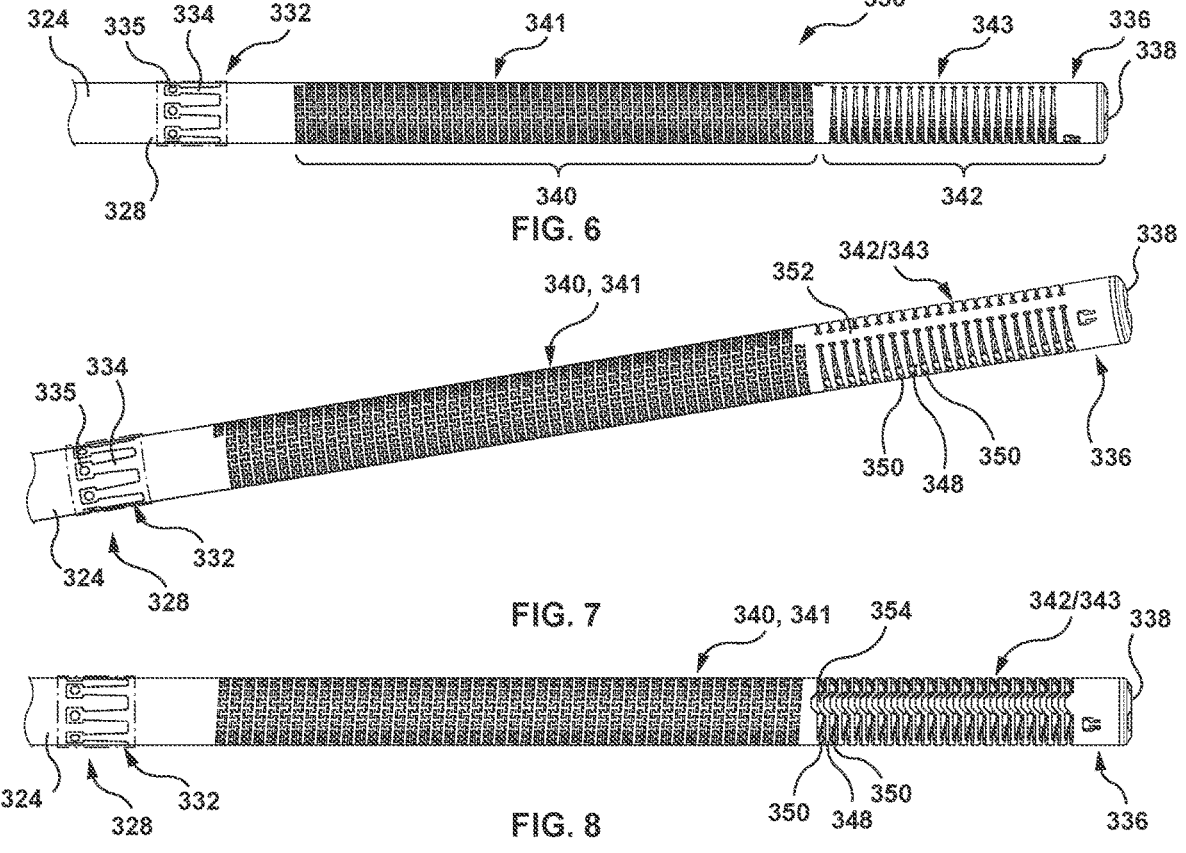
FIG. 6 is a side view of a distal portion of an inner steerable catheter of the delivery system of FIG. 3, wherein the inner steerable catheter is removed from the delivery system for sake of illustration.
FIG. 7 is a perspective view of the distal portion of the inner steerable catheter of the delivery system of FIG. 3, wherein the inner steerable catheter is removed from the delivery system for sake of illustration.
FIG. 8 is another side view of the distal portion of the inner steerable catheter of the delivery system of FIG. 3, wherein the inner steerable catheter is removed from the delivery system for sake of illustration.
Figure 12:
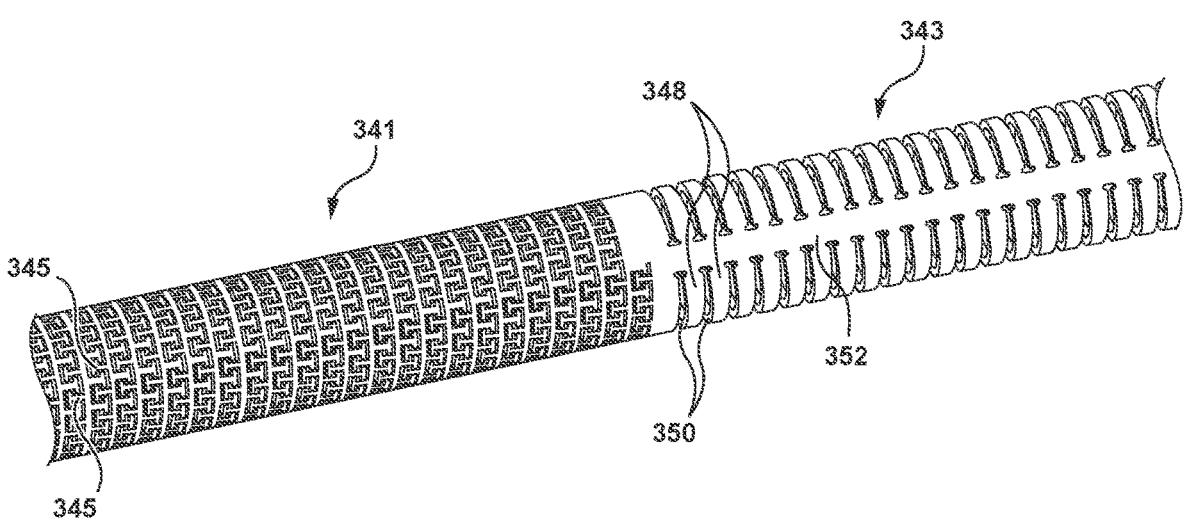
FIG. 12 is another perspective view of the inner distal flex component of the inner steerable catheter of FIG. 6, wherein the inner distal flex component is removed from the inner steerable catheter for sake of illustration.

Embodiments hereof relate to a delivery system 310 which may be used to deliver and deploy the prosthetic heart valve 100 disclosed herein to the heart of a patient. FIG. 3 illustrates a side view of the delivery system 310, and FIG. 3A is a cross-sectional view taken along line A-A of FIG. 3. FIG. 4 is an exploded view of the delivery system 310, and FIG. 5 illustrates the delivery system 310 with a distal portion thereof in situ. The delivery system 310 includes a distal sheath capsule 312 for housing at least a portion of the prosthetic heart valve 100, a flexible shaft 314 contained within and coupled to the distal sheath capsule 312, an inner steerable catheter 316 disposed over the flexible shaft 314, and an outer steerable catheter 318 disposed over the inner steerable catheter 316. The inner steerable catheter 316 includes a handle 317 at a proximal portion thereof for manipulation in situ, and the outer steerable catheter 318 includes a handle 319 at a proximal portion thereof for manipulation in situ. During delivery, the prosthetic heart valve 100 contained within the distal sheath capsule 312 is steered by the inner steerable catheter 316 and the outer steerable catheter 318 into alignment within the mitral valve for which the prosthetic heart valve 100 serves as a replacement. The inner steerable catheter 316 may be manipulated or steered independently from the outer steerable catheter 318, as will be described in more detail herein, and provides the delivery system 310 with omnidirectional steering capabilities to direct the distal sheath capsule 312. Particularly, the inner steerable catheter 316 may be axially translated and may be rotated up at least 90° relative to the outer steerable catheter 316 when one or both of the outer steerable catheter 318 and the inner steerable catheter 316 is in a flexed or bent configuration. Further, in an embodiment, the inner steerable catheter 316 may be axially translated and may be rotated 360° relative to the outer steerable catheter 316 when one or both of the outer steerable catheter 318 and the inner steerable catheter 316 is in a flexed or bent configuration.

When the prosthetic heart valve 100 is loaded into the distal sheath capsule 312, at least a portion of the valve brim 104 of the prosthetic heart valve 100 may protrude from the distal sheath capsule 312 prior to valve release. In an embodiment hereof, as depicted in FIG. 3, a suture 320 is disposed around the valve brim 104 to hold the valve brim 104 in a reduced diameter state for delivery. In this manner, the length of distal sheath capsule 312 is minimized and the distal sheath capsule 312 has a length less than the length of the prosthetic heart valve 100 in its reduced diameter state. The diameter of the valve brim 104 is radially compressed and minimized by the suture 320, and the distal sheath capsule 312 has a diameter greater than a diameter of the prosthetic heart valve 100 in its reduced diameter state. When radially compressing the valve brim 104, the suture 320 also provides a tapered shape to the valve brim 104 for crossing through the septal opening during delivery and/or recapture, as will be described in more detail herein.

In an embodiment, as shown in FIG. 5, the delivery system 310 is delivered to the target site via an introducer sheath 511 having a hemostasis valve on a proximal end thereof. In an embodiment, the target site is a native mitral valve and the introducer sheath 511 is tracked to the right atrium via the inferior vena cava. The introducer sheath may be used to make a transeptal entry into the left atrium across the septum. The introducer sheath 511 may be subsequently withdrawn after the delivery system 310 is positioned across the septum. The introducer sheath 511 may be steerable or pre-shaped in a configuration suitable for the particular approach to the target valve.

Components of the delivery system 310 will now be described in more detail. At a proximal end thereof, as best shown in the exploded view of FIG. 4, the flexible shaft 314 is fixedly secured to a manifold 315. At a distal end thereof, the flexible shaft 314 is contained within and coupled to the distal sheath capsule 312, which houses at least a portion of the prosthetic heart valve 100 during delivery. More particularly, the distal sheath capsule 312 functions to protect, secure, and compressively retain the anchoring member 102B and valve support 102A of the prosthetic heart valve 100 in a reduced diameter state for delivery to a treatment site. The distal sheath capsule 312 is concentrically disposed over a distal end of the flexible shaft 314, and an annular cavity (not shown) is defined between an inner surface of the distal sheath capsule 312 and an outer surface of the flexible shaft 314. The flexible shaft 314 and the distal sheath capsule 312 together house a hydraulic deployment system (not shown) that is configured to cause proximal and distal translation of the distal sheath capsule 312 with respect to the prosthetic heart valve 100 for deployment. The flexible shaft 314 contains or houses a hydraulic tube or lumen (not shown) that is in fluid communication with the annular cavity and functions to deliver a fluid to hydraulically actuate the distal sheath capsule 312. The distal sheath capsule 312 is configured to be distally advanced relative to the flexible shaft 314 to release and deploy the anchoring member 102B and the valve support 102A of the prosthetic heart valve 102 from distal sheath capsule 312. Via the manifold 315, fluid is injected through the flexible shaft 314 in order to drive the distal sheath capsule 312 distally. The prosthetic heart valve 100 may remain in a stationary longitudinal position relative to the native valve while the distal sheath capsule 312 is driven distally, thereby increasing the precision of deployment. Hydraulic valve delivery systems consistent with embodiments hereof include, for example, those described in U.S. Pat. No. 9,034,032 to McLean et al., International Patent Application No. PCT/US5114/029549 to McLean et al., and U.S. Pat. No. 10,561,497 to Duffy et al., which are hereby incorporated by reference in their entirety.

The inner steerable catheter 316 is disposed over the flexible shaft 314 such that an annular lumen 322 (shown on FIG. 3A) is defined between an outer surface of the flexible shaft 314 and an inner surface of the inner steerable catheter 316 along an entire length of the inner steerable catheter 316. The flexible shaft 314 is slidingly disposed within the inner steerable catheter 316 such that relative axial movement is permitted therebetween as will be described in more detail below. As used herein, "slidably" generally denotes back and forth movement in a longitudinal direction along or generally parallel to a central longitudinal axis LA of the delivery system 310.

In an embodiment, the proximal end of the handle 317 of the inner steerable catheter 316 is attached to a distal end of the manifold 315 of the flexible shaft 314 to form a handle subassembly 311. The handle subassembly 311 couples the inner steerable catheter 316 to the flexible shaft 314 so as to form a subassembly of the inner steerable catheter 316 and the flexible shaft 314 which can be manipulated and moved relative to the outer steerable catheter 318, as will be described in more detail herein. In an embodiment, the manifold 315 is attached to the handle 317 so as to permit controlled axial movement of the flexible shaft 314 relative to the inner steerable catheter 316 along a telescoping portion 313, with interfacing geometry to reduce or inhibit rotational motion between the flexible shaft 314 and the inner steerable catheter 316. More particularly, along the telescoping portion 313, the proximal end of the handle 317 slides within the distal end of the manifold 315. In an embodiment, the handle 317 is attached to the manifold 315 so that no relative rotational movement is permitted between the inner steerable catheter 316 to the flexible shaft 314. Rather, due to the handle subassembly 311, the subassembly of the inner steerable catheter 316 and the flexible shaft 314 rotate together when either of the handle 317 or the manifold 315 is rotated. Rotational motion between the manifold 315 and the handle 317 may be prevented by the inclusion of mating or interfacing geometry along the telescoping portion 313, and functions to prevent relative rotation between the manifold 315 and the handle 317. For example, along the telescoping portion 313, the mating or interfacing geometry may include an elongated rib (not shown) formed on an outer surface of the proximal end of the handle 317 that is slidingly received within a groove (not shown) formed on an inner surface of the distal end of the manifold 315. Such mating or interfacing geometry prevents relative rotation between the handle 317 and the manifold 315 (and thus between the inner steerable catheter 316 and the flexible shaft 314), but permits relative axial movement between the handle 317 and the manifold 315 (and thus between the inner steerable catheter 316 and the flexible shaft 314) because the elongated rib is permitted to slide back and forth within the mating geometry of the groove. The amount of relative axial movement that is permitted between the flexible shaft 314 and the inner steerable catheter 316 is limited or controlled by a length of the telescoping portion 313 at a proximal end of the handle 317. The flexible shaft 314 may be moved back and forth relative to the inner steerable catheter 316 along the telescoping portion 313 and the amount of relative axial movement that is permitted between the flexible shaft 314 and the inner steerable catheter 316 is equal to the length of the telescoping portion 313. Although described above with telescoping portion 313 and interfacing geometry to achieve the desired relative movement between the handle 317 and the manifold 315 (and thus the flexible shaft 314 and the inner steerable catheter 316), the handle 317 may be attached to the manifold 315 in any suitable manner that would achieve the desired relative movement between the flexible shaft 314 and the inner steerable catheter 316, as would be understood by one of ordinary skill in the art. Further, in another embodiment hereof, the handle subassembly 311 may be modified such that relative rotation is permitted between the inner steerable catheter 316 and the flexible shaft 314.

The inner steerable catheter 316 includes a flexible, steerable tubular component or shaft 324, the handle 317 fixedly secured to a proximal end 326 of the shaft 324, an inner distal flex component 330 extending distally from a distal end 328 of the shaft 324 and including a first cut pattern 341 and a second cut pattern 342, and a first pullwire 358. The handle 317 includes an actuator 317A that is accessible to the user and may be manipulated to control flexing or bending of the inner distal flex component 330 of the shaft 324. More particularly, as will be explained in more detail herein, the first pullwire 358 is attached to and extends between the handle 317 and the inner distal flex component 330. The first pullwire 358 is selectively tensioned by the user to bend the inner distal flex component 330. The inner steerable catheter 316 is configured to transition between a non-flexed configuration when the first pullwire 358 is not tensioned and a flexed configuration in which the first pullwire 358 is tensioned. In the non-flexed configuration, tension is not applied to the first pull wire 358 and the inner distal flex component 330 is in its as-formed shape or configuration. Stated another way, when in the non-flexed configuration, the shape of inner distal flex component 330 is not determined by tension applied by the first pullwire 358. In an embodiment, when in the non-flexed configuration, the inner distal flex component 330 may be straight, i.e., not curved or bent, and coaxial with the shaft 324. In an embodiment, when in the non-flexed configuration, the inner distal flex component 330 may be substantially straight but may include a slight, pre-formed curve or bend therein, with any such curve or bend not being caused by tension applied by the first pullwire 358. In the flexed configuration, tension is applied to the first pullwire 358 and the tensioned first pullwire 358 causes the inner distal flex component 330 to curve or bend along a portion thereof as will be described in more detail herein. The dimension of the curvature of the inner distal flex component 330 in the flexed configuration depends upon the target anatomy for use of the delivery system 310, and/or the size or profile of the delivery system 310. In an embodiment in which the delivery system 310 is utilized in a transcatheter mitral valve implantation procedure, the radius of curvature of the inner distal flex component 330 in the flexed configuration ranges between twenty-five (25) millimeters and sixty (60) millimeters.

The shaft 324 may be formed of one or more polymeric materials, non-exhaustive examples of which include polyethylene, polyethylene block amide copolymer (PEBA), polyamide and/or combinations thereof, either laminated, blended or co-extruded. Optionally, the shaft 324 or some portion thereof may be formed as a composite having a reinforcement layer incorporated within a polymeric body in order to enhance strength and/or flexibility and/or torquability. Suitable reinforcement layers include braiding, wire mesh layers, embedded axial wires, embedded helical or circumferential wires, hypotubes, and the like. In one embodiment, for example, at least a proximal portion of the shaft 324 may be formed from a reinforced polymeric tube.

The structure of the inner distal flex component 330 will now be described in more detail with respect to FIGS. 6-12, which illustrate various enlarged views of the inner distal flex component 330. The inner distal flex component 330 is a laser cut metallic tubular component and includes a proximal end 332 and a distal end 336. In an embodiment, the inner distal flex component 330 is formed from a laser cut hypotube. The inner distal flex component 330 may be formed from stainless steel or a nickel titanium alloy such as NITINOL. Further, in an embodiment hereof, the inner distal flex component 330 does not include any polymeric material, such as a polymeric coating or jacket, except at the proximal end 332 thereof in order to bond the proximal end 332 of the inner distal flex component 330 to a distal end of the shaft 324. The proximal end 332 of the inner distal flex component 330 is configured for mounting and fixedly attaching to the distal end 328 of the shaft 324 and in some constructions includes a plurality of circumferentially-spaced fingers 334, each terminating at a proximal end 335. In some constructions, the proximal end 335 of each of the fingers 334 can have an enlarged width as shown. Regardless, the circumferentially-spaced fingers 334 are readily interposed within or over the distal end 328 of the shaft 324 so as to facilitate attachment thereto (e.g., adhesive bond, heated fusing, etc.). The distal end 336 of the inner distal flex component 330 includes an end cap 338 attached thereto.

The inner distal flex component 330 includes a first longitudinal portion 340 in which a sidewall of the inner distal flex component 330 has a first cut pattern 341 and a second longitudinal portion 342 in which the sidewall of the inner distal flex component 330 has a second cut pattern 343 that is different from the first cut pattern 341. The first cut pattern 341 and the second cut pattern 342 are integrally formed on the inner distal flex component 330 and the inner distal flex component 330 is a continuous tubular component having a consistent outer diameter along the entire length thereof. The first longitudinal portion 340 is disposed proximal to the second longitudinal portion 342. In an embodiment, the first longitudinal portion 340 is longer than the second longitudinal portion 342. More particularly, the first longitudinal portion 340 is approximately twice as long as the second longitudinal portion 342. In an embodiment, the length of the first longitudinal portion 340 is between 50 mm and 70 mm, and the length of the second longitudinal portion 342 is between 25 mm and 35 mm.

The first longitudinal portion 340 is longitudinally disposed between the proximal end 332 of the inner distal flex component 330 and the second longitudinal portion 342. The first longitudinal portion 340 includes the first cut pattern 341 that includes a plurality of generally circumferentially extending ribs 345 separated, or demarcated, by a single, continuous helical slot 344, such that generally each rib 345 is separated from an adjacent rib 345 via windings of the helical slot 344. The plurality of ribs 345 substantially extend in a circumferential direction around the central longitudinal axis of the inner distal flex component 330. The plurality of ribs 345 of the inner distal flex component 330 are shown in embodiments described above as having a uniform pitch. Stated another way, each rib of the plurality of ribs 345 have the same width. The plurality of ribs 345 and the helical slot 344 are formed via laser-cutting the inner distal flex component 330 and the configuration of the laser cut pattern is configured to impart non-kinking flexibility to the inner distal flex component 330.

The helical slot 344 is circumferentially continuous, and spirals or winds around the inner distal flex component 330 along a length of the first longitudinal portion 340. The helical slot 344 has a non-linear path that results in each rib 345 including a plurality of alternating T-shaped protrusions 346A, 346B. T-shaped protrusions 346A are oriented with a base thereof closer to the distal end 336 of the inner distal flex component 330, while T-shaped protrusions 346B are oriented with a base thereof closer to a proximal end 332 of the inner distal flex component 330. A T-shaped protrusion 346B is disposed between each pair of adjacent T-shaped protrusions 346A, and a T-shaped protrusion 346A is disposed between each pair of adjacent T-shaped protrusions 346B. Adjacent ribs 345 nest within each other, with the T-shaped protrusions 346A of a rib 345 being disposed between a pair of two T-shaped protrusions 346B of a directly adjacent proximal rib 345. The first cut pattern 341 allows the first longitudinal portion 340 to be axially stretched and/or contracted, because the ribs 345 are configured to nest within each other. The width of the helical slot 344 is configured to decrease when a compressive or compression force is applied to the inner distal flex component 330 and the width of the helical slot 344 is configured to increase when a tensive or tension force is applied to the inner distal flex component 330.

Since the first cut pattern 341 allows the first longitudinal portion 340 to be axially stretched and/or contracted, the column strength of the first longitudinal portion 340 transitions between different values depending upon the compressive force placed on it longitudinally, i.e., in the longitudinal or axial direction. More particularly, the first longitudinal portion 340 includes a free state in which it is floppy when no longitudinal compressive force is exerted upon it. In the free state, the first longitudinal portion 340 has a first column strength. The first longitudinal portion 340 includes a second state in which it is self-standing or self-supporting or rigid when sufficiently compressed in a longitudinal direction. In the second state, the first longitudinal portion 340 has a second column strength that is greater than the first column strength and the second column strength is sufficient to maintain axial alignment along its length. The first longitudinal portion 340 transitions from floppy in the free state to self-standing or rigid in the second state when a sufficient longitudinal compressive force is exerted upon it.

Tensioning of the first pullwire 358 controls or dictates the column strength of the first longitudinal portion 340, and exerts a sufficient compressive force onto the first longitudinal portion 340 to transition it between the free and second states described above. As such, the first longitudinal portion 340 is in the free state when the inner steerable catheter 316 is in its non-flexed configuration and the first longitudinal portion 340 is in the second state when the inner steerable catheter 316 is in its flexed configuration. When the first longitudinal portion 340 is in the free state, it has insufficient column strength to be self-standing or to maintain axial alignment along its length. When the first pullwire 358 is tensioned, a compressive force is placed on the first longitudinal portion 340. When the first pullwire 358 is sufficiently tensioned, the first longitudinal portion 340 transitions to the second state and has sufficient column strength to be self-standing and the second longitudinal portion 342 has a curved configuration as described in more detail herein. When the first longitudinal portion 340 is in the second or self-standing state, the second longitudinal portion 342 can bend or curve without changing or substantially/significantly changing the curvature of the first longitudinal portion 340. In addition, when the first longitudinal portion 340 is in the second state, a force can be applied to bend it (i.e., by bending or flexing of the outer steerable catheter 318) and when that force is removed, the first longitudinal portion 340 tends to resume the second state it had before the bending force was applied thereto.

The second longitudinal portion 342 is longitudinally disposed between the distal end 336 of the inner distal flex component 330 and the first longitudinal portion 340. The second longitudinal portion 342 includes the second cut pattern 343 that includes a plurality of generally circumferentially extending ribs 348 separated, or demarcated, by a plurality of generally circumferentially extending slots 350, such that generally each rib 348 is separated from an adjacent rib 348 by a slot 350. The plurality of ribs 348 and the plurality of slots 350 substantially extend in a circumferential direction around the central longitudinal axis of the inner distal flex component 330. The plurality of ribs 348 and the plurality of slots 350 are formed via laser-cutting the inner distal flex component 330 and the configuration of the laser cut pattern is configured to impart non-kinking flexibility to the inner distal flex component 330 that allows the inner distal flex component 330 to bend when the first pullwire 358 is selectively tensioned, thereby reducing the pulling force required for bending the inner distal flex component 330.

Longitudinally adjacent ones of the ribs 348 are separated by a slot 350. The slots 350 are circumferentially discontinuous, extending between 300° and 350°. As such, slots 350 are approximately parallel to each other but are separated from one another. Thus, the cut pattern establishes a longitudinal spine 352. The plurality of ribs 348 of the inner distal flex component 330 are shown in embodiments described above as having a uniform pattern. Stated another way, each rib of the plurality of ribs 348 has the same width. The discontinuous slots 350 and the spine 352 generally connect or maintain adjacent ones of the ribs 348 relative to one another, yet permit transverse articulation so that the inner distal flex component 330 is bendable via the first pullwire 358. Other constructions that promote desired transverse articulation are also envisioned. While being flexible for requisite bending or articulation (due to a material strength, thickness, and circumferential width), the spine 352 in combination with the ribs 348 provide a longitudinal stability for sliding the inner distal flex component 330 in an axial direction relative to the flexible shaft 314. The spine 352 in combination with the ribs 348 impart circumferential or radial rigidity, yet permit or promote transverse articulation, designed to give the inner distal flex component 330 adequate axial and radial strength to prevent buckling or kinking when being bent or curved via tensioning of the first pullwire 358 as the inner distal flex component 330 is removed steered in situ through the vasculature.

Circumferentially opposing the spine 352, each rib 348 includes an integral curve or tooth 354 formed thereon that extends generally towards the proximal end 332 of the inner distal flex component 330. Adjacent ribs 348 nest within each other, with the tooth 354 of a rib 348 being disposed within the tooth 354 of a directly adjacent proximal rib 348. The teeth 354 improve torqueability of the inner distal flex component 330 when the inner distal flex component is in its flexed configuration as described in more detail herein, because more torque is translated via the teeth 354 when the teeth 354 nest or abut against each other when the inner distal flex component is in its flexed configuration. In addition, the second cut pattern includes a plurality of cross-struts 356. Each cross-strut 356 extends from a tooth 354 of a rib 348 to a directly adjacent proximal rib 348. In an embodiment, exactly two cross-struts 356 extend between each tooth 354 and a directly adjacent proximal rib 348 and the exactly two cross-struts 356 extent from opposing sides of the tooth 354. The cross-struts 356 improve torqueability of the inner distal flex component 330, especially when the inner distal flex component 330 is in the non-flexed configuration and the teeth 354 are not engaged or nested against each other. The cross-struts 356 also increase longitudinal stability or rigidity along the second longitudinal portion 342.

Figure 13:
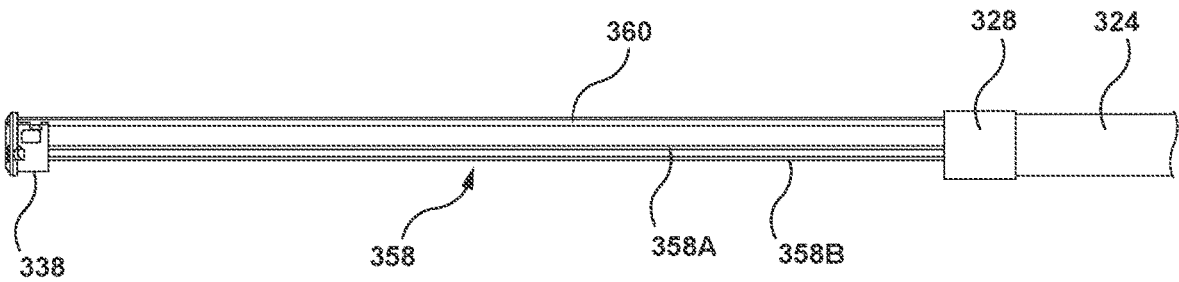
FIG. 13 is a side view of the distal portion of the inner steerable catheter of FIG. 6 without the inner distal flex component, which is removed for sake of illustration.

As previously stated, the inner steerable catheter 316 also includes the first pullwire 358 which is attached to and extends between the handle 317 of the inner steerable catheter 316 and the inner distal flex component 330 of the inner steerable catheter 316. The first pullwire 358 is formed from stainless steel or Nitinol. The first pullwire 358 is selectively tensioned by the user to bend or curve the inner distal flex component 330 to the flexed configuration. The first pullwire 358 is best shown in FIG. 3A, which is a cross-sectional view taken along A-A of FIG. 3, and in FIGS. 13 and 14, which illustrate the distal portion of the inner steerable catheter 316 with the inner distal flex component 330 removed for sake of illustration only. The first pullwire 358 is a single, continuous elongated component that, when placed within the delivery system 310, integrally includes a first leg 358A, a second leg 358B, and a loop 358C formed therebetween the first and second legs 358A, 358B. The proximal ends of the first and second legs 358A, 358B are coupled to the actuator 317A of the handle 317. As best shown in FIG. 13, the loop 358C is coupled to the cap 338 that is fixedly secured to the distal end 336 of the inner distal flex component 330. With reference to FIGS. 15A and 15B, the cap 338 is an annular component that includes a first opening 337 and a second opening 339 formed through a sidewall thereof. The second opening 339 includes an integral ledge 339A formed therein. Each of the first leg 358A and the second leg 358B extends within the second opening 339 of the cap 338, and the loop 358C of the first pullwire 358 extends or loops around ledge 339A to couple the first pullwire 358 to the cap 338, and thereby couple the first pullwire 358 to the inner distal flex component 330. The connection between the first pullwire 358 and the cap 338 is thus weldless or weld-free, which is advantageous as welded connections are a point of weakness when tension is applied to the first pullwire 358. In addition, since the first pullwire 358 includes legs 358A, 358B extending between the handle 317 and the inner distal flex component 330, the strength of the first pullwire 358 is increased relative to a pullwire having only a single strand or leg between the handle and the inner distal flex component.

In addition, the first pullwire 358 is not constrained within a dedicated tube or lumen within the delivery system 310. As shown in FIG. 3A, each of the first leg 358A and the second leg 358B extends within the annular lumen 322 defined between an outer surface of the flexible shaft 314 and an inner surface of the inner steerable catheter 316. The first pullwire 358 thus extends alongside or adjacent to the inner surface of the inner distal flex component 330 and alongside or adjacent to the inner surface of the shaft 324 for the entire length of the inner steerable catheter 316. Since the first pullwire 358 is not constrained within a dedicated tube or lumen within the delivery system 310, friction is minimized when the first pullwire 358 is tension is applied thereto. The first pullwire 358 can freely move in a circumferential direction within the annular lumen 322, thereby allowing more bending freedom or omnidirectional bending. More particularly, the first pullwire 358 is arranged or disposed in the channel such that a portion thereof can freely move in a circumferential direction along the first and second longitudinal portions 340, 342 of the inner distal flex component 330. In an embodiment, the first pullwire 358 is arranged in the annular channel or lumen 322 such that a portion thereof can freely move 360 degrees in a circumferential direction within the annular lumen 322.

The handle 317 includes the actuator 317A for tensioning the first pullwire 358. The handle 317 can have any shape or size appropriate for convenient handling by a user. The actuator 317A is coupled to the proximal ends of the legs 358A, 358B of the first pullwire 358, and is generally constructed to provide selective proximal retraction and distal advancement of the first pullwire 358. Stated another way, the actuator 317A is coupled to the proximal ends of the legs 358A, 358B of the first pullwire 358 and is constructed to selectively push or pull the first pullwire 358. The actuator 317A may assume any construction that is capable of providing the desired pullwire actuation functionality. In an embodiment, the actuator 317A is configured as a rotatable knob that is rotated in a first direction (i.e., clockwise) to proximally retract the first pullwire 358 and apply tension thereto, and is rotated in a second, opposing direction (i.e., counter-clockwise) to distally advance the first pullwire 358 and remove or release tension therefrom, such as the rotatable knob described in U.S. Pat. No. 10,188,833 to Bolduc et al., filed Dec. 8, 2015, or the rotatable knob described in U.S. Pat. No. 6,607,496 to Poor et al., filed on September 12, each of which is assigned to the same assignee as the present disclosure and which is herein incorporated by reference in its entirety. In another embodiment, the actuator 317A may be configured as a button such as those described in U.S. Pat. No. 10,278,852 to Griffin, filed on Mar. 10, 2016, which is assigned to the same assignee as the present disclosure and which is herein incorporated by reference in its entirety.

Tension is applied to the first pullwire 358 in order to bend the inner distal flex component 330 as desired and thereby steer the delivery system 310 within the vasculature as the delivery system 310 is removed advanced through the vasculature to the treatment site. When tension is initially applied to the first pullwire 358, a compressive load is applied to the first longitudinal portion 340 of the inner distal flex component 330 and the first longitudinal portion 340 transitions from the free state (i.e., floppy) to the second state (i.e., self-standing or rigid) as described above. As tension is further applied to the first pullwire 358, the inner distal flex component 330 begins to bend or curve along the second longitudinal portion 342 while the first longitudinal portion 340 remains in the second state. In an embodiment, the second longitudinal portion 342 is configured to bend or curve up to 90 degrees. In another embodiment, the second longitudinal portion 342 is configured to bend or curve greater than 90 degrees. Further, in another embodiment, the second longitudinal portion 342 is configured to bend or curve up to 360 degrees as tension is continued to be applied to the first pullwire 358. However, as will be understood by one of ordinary skill in the art, the degree of bending or curving of the second longitudinal portion 342 depends upon the length of the second longitudinal portion 342 and relatively longer lengths are required to enable bending or curving of the second longitudinal portion 342 up to 360 degrees. When the first longitudinal portion 340 is in the second state and the second longitudinal portion 342 is bent or curved by the first pullwire 358, the inner steerable catheter 316 is in its flexed configuration. Conversely, when the first longitudinal portion 340 is in the free state and the second longitudinal portion 342 is not bent or curved by the first pullwire 358, the inner steerable catheter 316 is in its non-flexed configuration.

Figure 14:
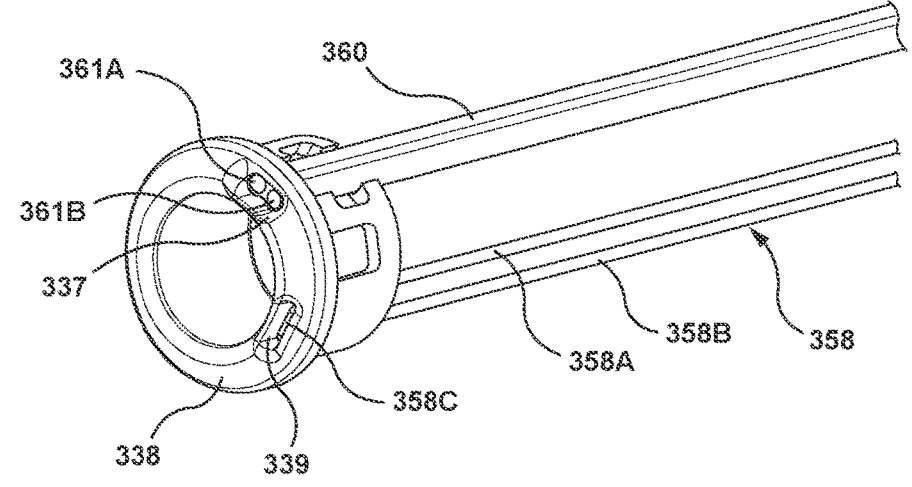
FIG. 14 is an end perspective view of FIG. 13.
Figures 15A, 15B:
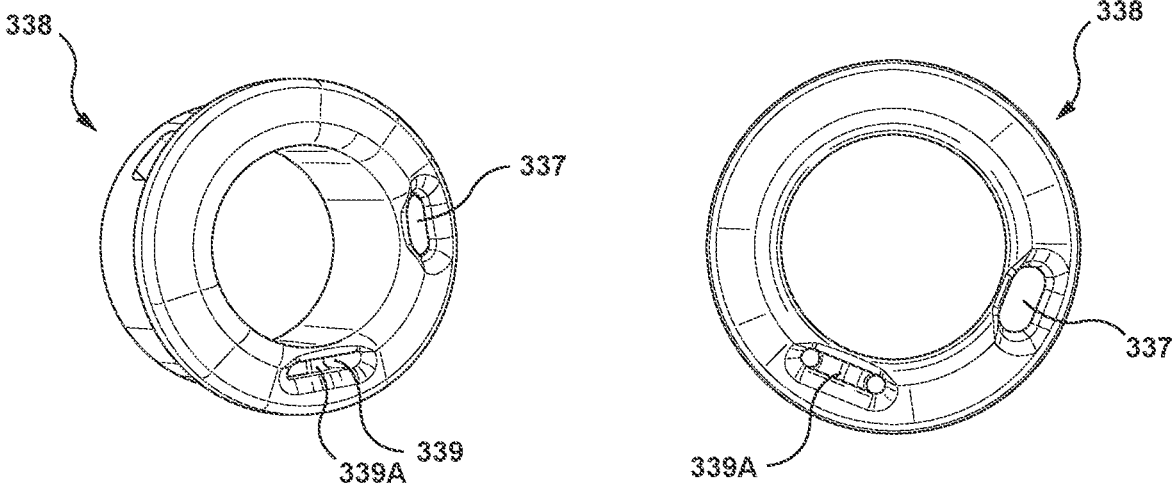
FIG. 15A is a perspective view of an end cap of the inner steerable catheter of FIG. 6, where the end cap is removed from the inner steerable catheter for sake of illustration.
FIG. 15B is an end view of the end cap of the inner steerable catheter of FIG. 6, where the end cap is removed from the inner steerable catheter for sake of illustration.

With further reference to FIGS. 13 and 14, the delivery system 310 also includes a dual lumen tube 360 for housing the suture 320. As stated above, the suture 320 is disposed around the valve brim 104 to hold the valve brim 104 in a reduced diameter state for delivery. The operation and function of suture 320 will be described in more detail herein with reference to FIGS. 24-28. As shown in FIG. 3A, the dual lumen tube 360 extends between the handle 317 of the inner steerable catheter 316 and the cap 338 at the distal end 336 of the inner distal flex component 330. The dual lumen tube 360 extends within the annular lumen 322 defined between an outer surface of the flexible shaft 314 and an inner surface of the inner steerable catheter 316. The dual lumen tube 360 thus extends alongside or adjacent to the inner surface of the inner distal flex component 330 and alongside or adjacent to the inner surface of the shaft 324 for the entire length of the inner steerable catheter 316. A proximal end (not shown) of the dual lumen tube 360 is fixedly secured to the handle 317 and does not move relative thereto. As best shown in FIG. 13, a distal end of the dual lumen tube 360 is disposed within the first aperture 337 of the cap 338 and is fixedly secured to the cap 338 so that it does not move relative thereto.

The dual lumen tube 360 includes a first lumen 361A and a second lumen 361B which each extend a full length of the inner steerable catheter 316. The suture 320 is a single, continuous elongated component that, when placed within the delivery system 310, integrally includes a first leg 320A, a second leg 320B, and a loop 320C formed therebetween the first and second legs 320A, 320B. The proximal ends of the first and second legs 320A, 320B extend proximally out of the handle 317, as shown in FIG. 5, so as to be accessible to the user. The first leg 320A of the suture 320 extends through the first lumen 361A of the dual lumen tube 360, and the second leg 320B of the suture 320 extends through the second lumen 361B of the dual lumen tube 360. Separate or dedicated lumens 361A, 361B for each leg 320A, 320B of the suture 320 reduces twisting, entanglement, and friction of the suture legs within the delivery system 310. The loop 320C of the suture 320 is disposed distally of the distal end of the dual lumen tube 360, and extends around the valve brim 104 of the prosthetic heart valve 100, as will be described in more detail herein with reference to FIG. 25 and FIG. 28. The loop 320C of the suture 320 encircles or extends circumferentially around the valve brim 104 of the prosthetic heart valve 100 and is configured to hold the valve brim 104 in a reduced diameter state for delivery to the treatment site. As will be explained in more detail with respect to FIGS. 29-33, the suture 320 is removed from the prosthetic heart valve 100 by pulling on one end of the suture 320 (either the end associated with the first leg 320A or the end associated with second leg 320B) until the entire suture 320 is pulled through and removed from the delivery system 310. Due to the loop 320 that cinches the valve brim 104, the delivery system 310 beneficially does not include or require a long retractable capsule 312 for compressing the full length of the prosthetic heart valve 100, and therefore may be more efficiently utilized within the confines of native anatomy having small or restricted space such as but not limited to the left atrium and/or the left ventricle. Thus, the distal sheath capsule 312 compressively holds or retains the outflow portion of the prosthetic heart valve 100 in a reduced diameter state for delivery, while the suture 320 compressively holds or retains the inflow portion of the prosthetic heart valve 100 in a reduced diameter state for delivery. The suture 320 is a single, continuous elongated component that runs from the handle 317 of the inner steerable catheter 316 to the valve brim 104 of the prosthetic heart valve 100, around the valve brim 104 of the prosthetic heart valve 100, and back from the prosthetic heart valve 100 to the handle 317 of the inner steerable catheter 316 so that both ends of the suture 320 are accessible to the user.

The suture 320 is releasable to permit the valve brim 104 of the prosthetic heart valve 100 to return to an expanded or deployed state. More particularly, pulling on one or both ends of the suture 320 controls constriction/compression of the valve brim 104 of the prosthetic heart valve 100 and releasing/removing the suture 320 controls expansion/deployment of the valve brim 104 of the prosthetic heart valve 100. In an embodiment, the suture 320 may be formed from a monofilament or plastic suture material, such as polypropylene.

The outer steerable catheter 318 is slidably disposed over the inner steerable catheter 316 such that an annular lumen 362 (shown on FIG. 3A) is defined between an outer surface of the inner steerable catheter 316 and an inner surface of the outer steerable catheter 318 along an entire length of the outer steerable catheter 318. The subassembly of the inner steerable catheter 316 and the flexible shaft 314 is slidingly disposed within the outer steerable catheter 318 such that relative axial movement is permitted therebetween. In an embodiment, the amount of relative axial movement that is permitted between the subassembly of the inner steerable catheter 316 and the flexible shaft 314 and the outer steerable catheter 318 is limited or controlled by the length of the outer steerable catheter 318. Proximal retraction of axial movement of the subassembly of the inner steerable catheter 316 and the flexible shaft 314 is restricted when the distal sheath capsule 312 abuts against or contacts the distal end of the outer steerable catheter 318, and distal advancement of the subassembly of the inner steerable catheter 316 and the flexible shaft 314 is restricted when a distal end of the handle 317 of the inner steerable catheter 316 abuts against or contacts the proximal end of the handle 319 of the outer steerable catheter 316.

In addition to relative axial movement, the subassembly of the inner steerable catheter 316 and the flexible shaft 314 is disposed within the outer steerable catheter 318 such that relative rotation is permitted therebetween. Stated another way, the subassembly of the inner steerable catheter 316 and the flexible shaft 314 may collectively be torqued or rotated while the outer steerable catheter 318 remains stationary. As will be described in more detail herein, it may be necessary to torque or rotate the subassembly of the inner steerable catheter 316 and the flexible shaft 314 in order to properly position the distal sheath capsule 312 in situ. In an embodiment hereof, the subassembly of the inner steerable catheter 316 and the flexible shaft 314 is rotated or torqued via rotation of the handle subassembly 311 of the handle 317 and the manifold 315. The subassembly of the inner steerable catheter 316 and the flexible shaft 314 is operable to be rotated 360 degrees without kinking.

The outer steerable catheter 318 includes a flexible, steerable tubular component or shaft 364, the handle 319 fixedly secured relative to a proximal end 366 of the shaft 364, an outer distal flex component 370 extending distally from a distal end 368 of the shaft 364 and having a third cut pattern 369, and a second pullwire 390. The handle 319 includes an actuator 319A that is accessible to the user and may be manipulated to control steering of the outer distal flex component 370 of the shaft 364. More particularly, as will be explained in more detail herein, the second pullwire 390 is attached to and extends between the handle 319 and the outer distal flex component 370. The second pullwire 390 is selectively tensioned by the user to bend the outer distal flex component 370. The outer steerable catheter 318 is configured to transition between a non-flexed configuration when the second pullwire 390 is not tensioned and a flexed configuration in which the second pullwire 390 is tensioned. In the non-flexed configuration, tension is not applied to the first pull wire 358 and the outer distal flex component 370 is in its as-formed shape or configuration. Stated another way, when in the non-flexed configuration, the shape of outer distal flex component 370 is not determined by tension applied by the second pullwire 390. In an embodiment, when in the non-flexed configuration, the outer distal flex component 370 may be straight, i.e., not curved or bent, and coaxial with the shaft 324. In an embodiment, when in the non-flexed configuration, the outer distal flex component 370 may be substantially straight but may include a slight, pre-formed curve or bend therein, with any such curve or bend not being caused by tension applied by the second pullwire 390. In the flexed configuration, tension is applied to the second pullwire 390 and the tensioned second pullwire 390 causes the outer distal flex component 370 to curve or bend as will be described in more detail herein. The dimension of the curvature of the outer distal flex component 370 in the flexed configuration depends upon the target anatomy for use of the delivery system 310, and/or the size or profile of the delivery system 310. In an embodiment in which the delivery system 310 is utilized in a transcatheter mitral valve implantation procedure, the radius of curvature of the outer distal flex component 370 in the flexed configuration ranges between twenty-five (25) millimeters and sixty (60) millimeters.

The shaft 364 may be formed of one or more polymeric materials, non-exhaustive examples of which include polyethylene, polyethylene block amide copolymer (PEBA), polyamide and/or combinations thereof, either laminated, blended or co-extruded. Optionally, the shaft 364 or some portion thereof may be formed as a composite having a reinforcement layer incorporated within a polymeric body in order to enhance strength and/or flexibility and/or torquability. Suitable reinforcement layers include braiding, wire mesh layers, embedded axial wires, embedded helical or circumferential wires, hypotubes, and the like. In one embodiment, for example, at least a proximal portion of the shaft 364 may be formed from a reinforced polymeric tube.

Figure 16:
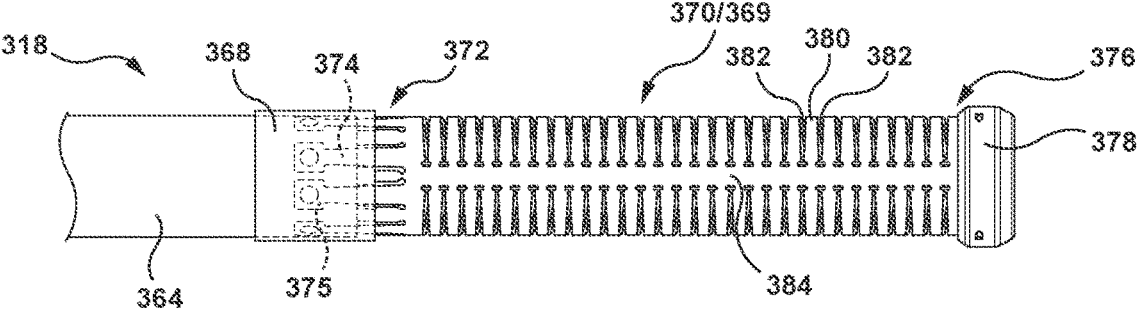
FIG. 16 is a side view of a distal portion of an outer steerable catheter of the delivery system of FIG. 3, wherein the outer steerable catheter is removed from the delivery system for sake of illustration.

The structure of the outer distal flex component 370 will now be described in more detail with respect to FIGS. 16-18, which illustrate various enlarged views of the outer distal flex component 370. The outer distal flex component 370 is a laser cut metallic tubular component and includes a proximal end 372 and a distal end 376. In an embodiment, the outer distal flex component 370 is formed from a laser cut hypotube. The outer distal flex component 370 may be formed from stainless steel or a nickel titanium alloy such as NITINOL. Further, in an embodiment hereof, the outer distal flex component 370 includes a polymeric material, such as a polymeric coating or jacket, along an entire length thereof. The proximal end 372 of the outer distal flex component 370 is configured for mounting and fixedly attaching to the distal end 368 of the shaft 364 and in some constructions includes a plurality of circumferentially-spaced fingers 374, each terminating at a proximal end 375. In some constructions, the proximal end 375 of each of the fingers 374 can have an enlarged width as shown. Regardless, the circumferentially-spaced fingers 374 are readily interposed within or over the distal end 368 of the shaft 364 so as to facilitate attachment thereto (e.g., adhesive bond, heated fusing, etc.). The distal end 376 of the outer distal flex component 370 includes an end cap 378 attached thereto.

The outer distal flex component 370 is a tubular component, and a sidewall of the outer distal flex component 370 has the third cut pattern 369. In an embodiment, the third cut pattern 369 is similar to the second cut pattern 343 of the inner distal flex component 330 of the inner steerable catheter 316. In another embodiment, the third cut pattern 369 is the different from the second cut pattern 343 of the inner distal flex component 330 of the inner steerable catheter 316. The third cut pattern 369 is integrally formed on the outer distal flex component 370 and the outer distal flex component 370 is a continuous tubular component having a consistent outer diameter along the entire length thereof. In an embodiment, the length of the third cut pattern 369 is less than the length of the first longitudinal portion 340 of the inner distal flex component 330 of the inner steerable catheter 316 and is greater than the length of the second longitudinal portion 342 of the inner distal flex component 330 of the inner steerable catheter 316. In an embodiment, the length of the third cut pattern 369 is between 40 mm and 50 mm.

The third cut pattern 369 includes a plurality of generally circumferentially extending ribs 380 separated, or demarcated, by a plurality of generally circumferentially extending slots 382, such that generally each rib 380 is separated from an adjacent rib 380 by a slot 382. The plurality of ribs 380 and the plurality of slots 382 substantially extend in a circumferential direction around the central longitudinal axis of the outer distal flex component 370. The plurality of ribs 380 and the plurality of slots 382 are formed via laser-cutting the outer distal flex component 370 and the configuration of the laser cut pattern is configured to impart non-kinking flexibility to the outer distal flex component 370 that allows the outer distal flex component 370 to bend when the second pullwire 390 is selectively tensioned, thereby reducing the pulling force required for bending the outer distal flex component 370.

Longitudinally adjacent ones of the ribs 380 are separated by a slot 382. The slots 382 are circumferentially discontinuous, extending between 300° and 350°. As such, slots 382 are approximately parallel to each other but are separated from one another. Thus, the cut pattern establishes a longitudinal spine 384. The plurality of ribs 380 of the outer distal flex component 370 are shown in embodiments described above as having a uniform pitch. Stated another way, each rib of the plurality of ribs 380 have the same width. The discontinuous slots 382 and the spine 384 generally connect or maintain adjacent ones of the ribs 380 relative to one another, yet permit transverse articulation so that the outer distal flex component 370 is bendable via the second pullwire 390. Other constructions that promote desired transverse articulation are also envisioned. While being flexible for requisite bending or articulation (due to a material strength, thickness, and circumferential width), the spine 384 in combination with the ribs 380 provide a longitudinal stability for sliding the outer distal flex component 370 in an axial direction relative to the flexible shaft 314. The spine 384 in combination with the ribs 380 impart circumferential or radial rigidity, yet permit or promote transverse articulation, designed to give the outer distal flex component 370 adequate axial and radial strength to prevent buckling or kinking when being bent or curved via tensioning of the second pullwire 390 as the outer distal flex component 370 is removed steered in situ through the vasculature.

Figure 17:
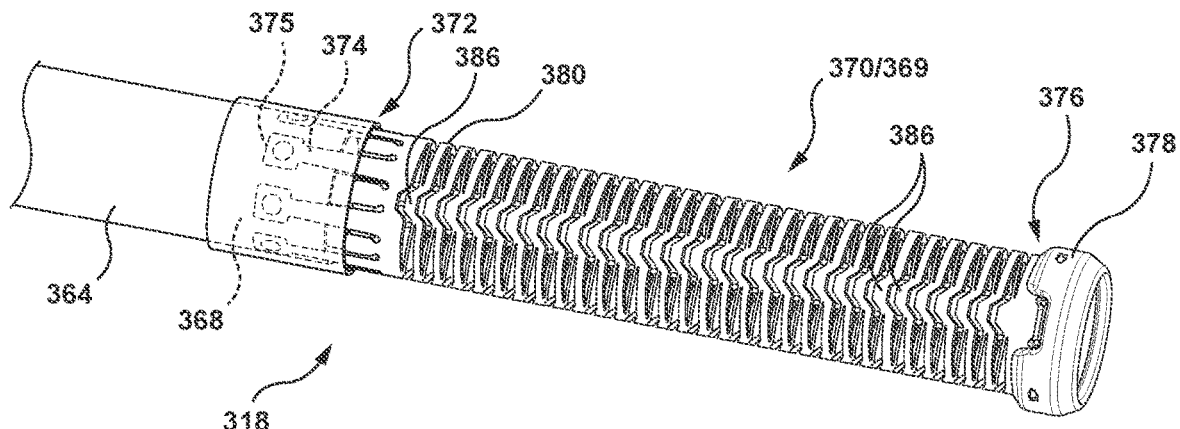
FIG. 17 is a perspective view of the distal portion of the outer steerable catheter of the delivery system of FIG. 3, wherein the outer steerable catheter is removed from the delivery system for sake of illustration.
Figure 18:
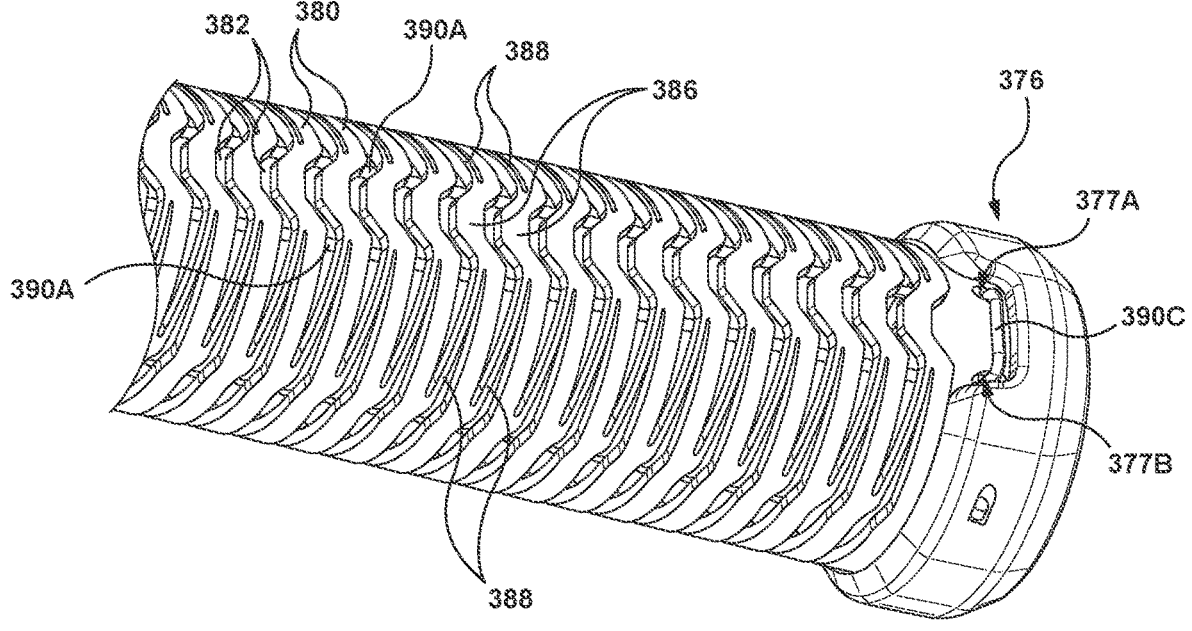
FIG. 18 is another enlarged perspective view of the distal portion of the outer steerable catheter of the delivery system of FIG. 3, wherein the outer steerable catheter is removed from the delivery system for sake of illustration and a third cut pattern of an outer distal flex component is shown.

As best shown on FIGS. 17 and 18, circumferentially opposing the spine 384, each rib 380 includes a tooth 386 formed thereon that extends generally towards the proximal end 372 of the outer distal flex component 370. Adjacent ribs 380 nest within each other, with the tooth 386 of a rib 380 being disposed within the tooth 386 of a directly adjacent proximal rib 380. The teeth 386 improve torqueability of the outer distal flex component 370 when the outer distal flex component is in its flexed configuration as described in more detail herein, because more torque is translated via the teeth 386 when the teeth 386 nest or abut against each other when the outer distal flex component is in its flexed configuration. In addition, as best shown on the enlarged view of FIG. 18, the second cut pattern includes a plurality of cross-struts 388. Each cross-strut 388 extends from a tooth 386 of a rib 380 to a directly adjacent proximal rib 380. In an embodiment, exactly two cross-struts 388 extend between each tooth 386 and a directly adjacent proximal rib 380 and the exactly two cross-struts 388 extent from opposing sides of the tooth 386. The cross-struts 388 improve torqueability of the outer distal flex component 370, especially when the outer distal flex component 370 is in the non-flexed configuration and the teeth 386 are not engaged or nested against each other. The cross-struts 388 also increase longitudinal stability or rigidity along the length of the outer distal flex component 370.

Figure 19:
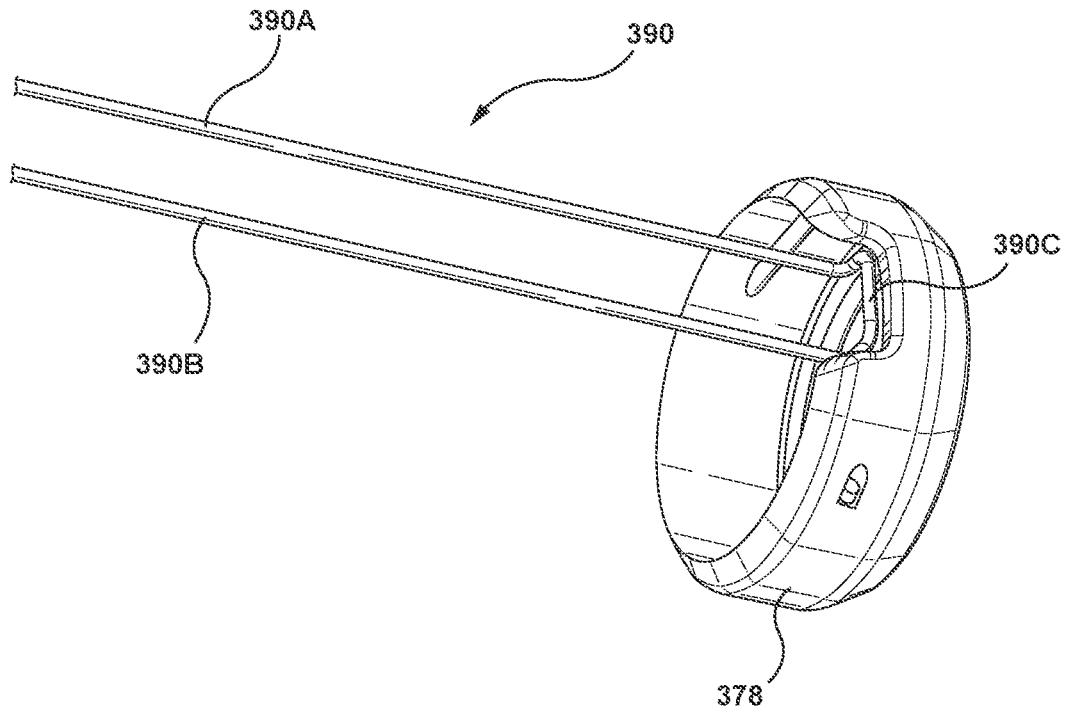
FIG. 19 is a perspective view of the distal portion of the outer steerable catheter of FIG. 18 without the outer distal flex component, which is removed for sake of illustration.

As previously stated, the outer steerable catheter 318 also includes the second pullwire 390 which is attached to and extends between the handle 319 of the outer steerable catheter 318 and the outer distal flex component 370 of the outer steerable catheter 318. The second pullwire 390 is formed from stainless steel of Nitinol. The second pullwire 390 is selectively tensioned by the user to bend the outer distal flex component 370 to the curved or flexed configuration. The second pullwire 390 is best shown in FIG. 3A, which is a cross-sectional view taken along A-A of FIG. 3, and in FIG. 19, which illustrate the distal portion of the outer steerable catheter 318 with the outer distal flex component 370 removed for sake of illustration only. The second pullwire 390 is a single, continuous elongated component that, when placed within the delivery system 310, integrally includes a first leg 390A, a second leg 390B, and a loop 390C formed therebetween the first and second legs 390A, 390B. The proximal ends of the first and second legs 390A, 390B are coupled to the actuator 319A of the handle 319. As best shown in FIG. 18, the loop 390C is coupled to the distal end 376 of the outer distal flex component 370.

The second pullwire 390 is not constrained within a dedicated tube or lumen within the delivery system 310. As shown in FIG. 3A, each of the first leg 390A and the second leg 390B extends within the annular lumen 362 defined between an outer surface of the inner steerable catheter 316 and an inner surface of the outer steerable catheter 318. The second pullwire 390 thus extends alongside or adjacent to the inner surface of the outer distal flex component 370 and alongside or adjacent to the inner surface of the shaft 364 for the entire length of the outer steerable catheter 318. Since the second pullwire 390 is not constrained within a dedicated tube or lumen within the delivery system 310, friction is minimized when the second pullwire 390 is tension is applied thereto. Similar to the first pullwire 358, the second pullwire 390 can freely move in a circumferential direction within the annular lumen 362, thereby allowing more bending freedom or omnidirectional bending.

Referring to FIG. 18, the distal end 376 of the outer distal flex component 370 includes two apertures 377A, 377B formed through the sidewall of the outer distal flex component 370. To couple the second pullwire 390 to the outer distal flex component 370, the first leg 390A of the pullwire 390 extends through the aperture 377A and the second leg 390B of the pullwire 390 extends through the aperture 377B, such that the loop 390C extends over an outer surface of the outer distal flex component 370 between the two apertures 377A, 377B, as shown on FIG. 18. Stated another way, the pullwire 390 is threaded through the two apertures 377A, 377B such that a portion of the pullwire 390 crosses over an outer surface of the outer distal flex component 370 between the two apertures 377A, 377B. The connection between the second pullwire 390 and the cap 378 is thus weldless or weld-free, which is advantageous as welded connections are a point of weakness when tension is applied to the second pullwire 390. In addition, since the second pullwire 390 includes legs 390A, 390B extending between the handle 319 and the outer distal flex component 370, the strength of the second pullwire 390 is increased relative to a pullwire having only a single strand or leg between the handle and the outer distal flex component.

The handle 319 includes the actuator 319A for tensioning the second pullwire 390. The handle 319 can have any shape or size appropriate for convenient handling by a user. The actuator 319A is coupled to the proximal ends of the legs 390A, 390B of the second pullwire 390, and is generally constructed to provide selective proximal retraction and distal advancement of the second pullwire 390. Stated another way, the actuator 319A is coupled to the proximal ends of the legs 390A, 390B of the second pullwire 390 and is constructed to selectively push or pull the second pullwire 390. The actuator 319A may assume any construction that is capable of providing the desired pullwire actuation functionality. In an embodiment, the actuator 319A is configured as a rotatable knob that is rotated in a first direction (i.e., clockwise) to proximally retract the second pullwire 390 and apply tension thereto, and is rotated in a second, opposing direction (i.e., counter-clockwise) to distally advance the second pullwire 390 and remove or release tension therefrom, such as the rotatable knob described in U.S. Pat. No. 10,188,833 to Bolduc et al., filed Dec. 8, 2015, or the rotatable knob described in U.S. Pat. No. 6,607,496 to Poor et al., filed on September 12, each of which is assigned to the same assignee as the present disclosure and which is herein incorporated by reference in its entirety. In another embodiment, the actuator 319A may be configured as a button such as those described in U.S. Pat. No. 10,278,852 to Griffin, filed on Mar. 10, 2016, which is assigned to the same assignee as the present disclosure and which is herein incorporated by reference in its entirety.

Tension is applied to the second pullwire 390 in order to bend the outer distal flex component 370 as desired and thereby steer the delivery system 310 within the vasculature as the delivery system 310 is removed advanced through the vasculature to the treatment site. When tension is applied to the second pullwire 390, the outer distal flex component 370 begins to bend or curve along the third cut pattern 369. In an embodiment, the outer distal flex component 370 is configured to bend or curve up to 90 degrees. In another embodiment, the outer distal flex component 370 is configured to bend or curve greater than 90 degrees. When the outer distal flex component 370 is bent or curved by the second pullwire 390, the outer steerable catheter 318 is in its flexed configuration. Conversely, when the outer distal flex component 370 is not bent or curved by the second pullwire 390, the outer steerable catheter 318 is in its non-flexed configuration. Notably, the outer distal flex component 370 is bent or curved by the second pullwire 390, the portion of the inner distal flex component 330 that is disposed under the outer distal flex component 370 is concurrently bent or curved by the outer distal flex component 370.

Figure 20:
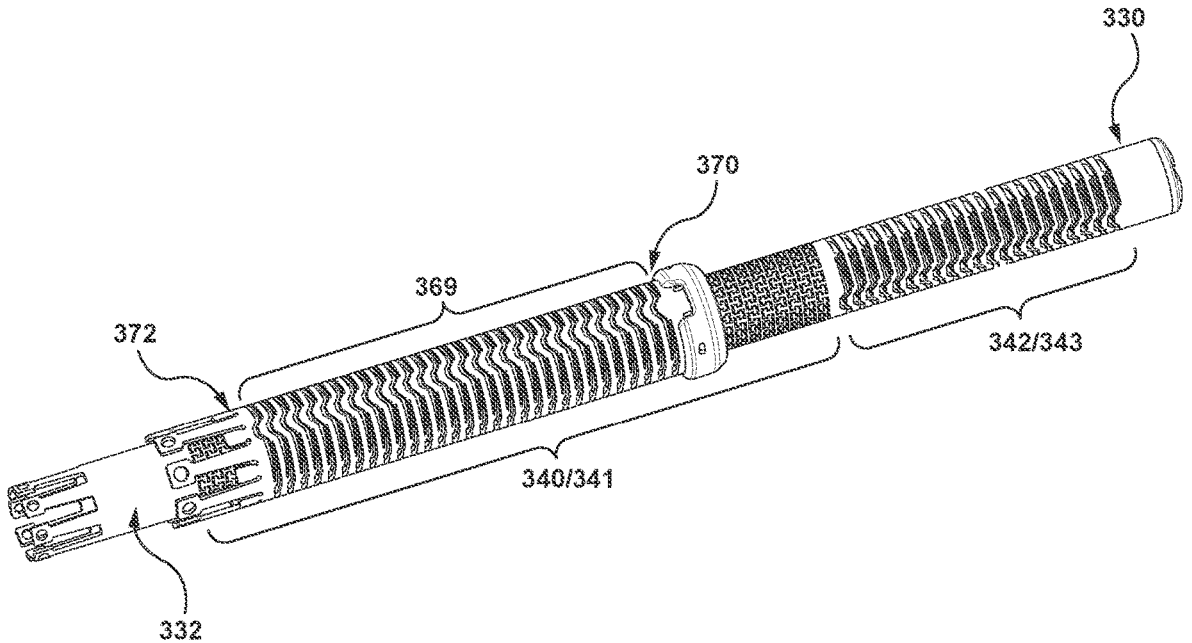
FIG. 20 is a perspective view of the outer distal flex component of the outer steerable catheter disposed over the inner distal flex component of the inner steerable catheter, where the outer and inner distal flex components are removed from the delivery system for sake of illustration.

Turning now to FIG. 20, the omnidirectional steering capabilities provided by the inner distal flex component 330 of the inner steerable catheter 316 and the outer distal flex component 370 of the outer steerable catheter 318 will be described in more detail. FIG. 20 illustrates the inner distal flex component 330 disposed within the outer distal flex component 370, with the rest of the delivery system 310 removed for sake of illustration. When the third cut pattern 369 of the outer distal flex component 370 is disposed over the first cut pattern 341 of the inner distal flex component 330, as shown in FIG. 20, the second cut pattern 343 of the inner distal flex component 330 may be bent or curved into the flexed configuration independently of the configuration of the outer steerable catheter 318. Further, due to the flexibility of the first cut pattern 341, the third cut pattern 369 of the outer distal flex component 370 may be bent or curved into the flexed configuration independently of the configuration of the inner steerable catheter 316. Thus, transitioning the inner steerable catheter 316 between its flexed and non-flexed configurations is independent from transitioning the outer steerable catheter 318 between its flexed and non-flexed configurations. In addition, with one or both of the inner steerable catheter 316 and the outer steerable catheter 318 in the flexed configuration, the inner steerable catheter 316 may be rotated or torqued a full 360 degrees relative to the outer steerable catheter 318 due to the flexibility of the first cut pattern 341 when the third cut pattern 369 of the outer distal flex component 370 is disposed over the first cut pattern 341 of the inner distal flex component 330. Thus, when in the flexed configuration, the second longitudinal portion 342 of the inner distal flex component 330 may travel a path of 360 degrees and beyond by continuously rotating the inner steerable catheter 316 about its axis. The first cut pattern 341 of the first longitudinal portion 340 is configured to permit compound bending and dual flex capability of the inner and outer steerable catheters 316, 318. The first cut pattern 341 of the first longitudinal portion 340 may be deflected or bent via the outer distal flex component 370 of the outer steerable catheter 318, while the second cut pattern 343 of the second longitudinal portion 342 may be independently curved or bent into the flexed configuration. Thus, the first cut pattern 341 of the first longitudinal portion 340 permits the outer distal flex component 370 and the inner distal flex component 330 to be independently selectively bent or curved. The curvature of the second cut pattern 343 of the second longitudinal portion 342 may be maintained while the third cut pattern 369 of the outer distal flex component 370 is curved or bent, and likewise the curvature of the third cut pattern 369 of the outer distal flex component 370 may be maintained while the second cut pattern 343 of the second longitudinal portion 342 is curved or bent. The dual flex capability of the inner and outer steerable catheters allow the user to easily manipulate the position of the distal capsule sheath 312 in situ so that the delivery system 310 can be properly positioned relative to the treatment site prior to deployment of the prosthetic heart valve. Independent or separate control of the steering capability of the inner and outer steerable catheters provide the user with more options to precisely position of the distal capsule sheath 312 in situ.

Figure 21A:
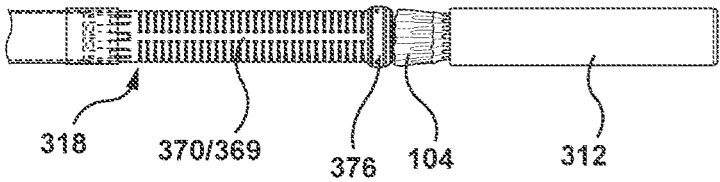
FIGS. 21A-21C illustrate relative axial movement between the inner steerable catheter and the outer steerable catheter, with each of the inner steerable catheter and the outer steerable catheter being in a non-flexed configuration.
Figure 21B:
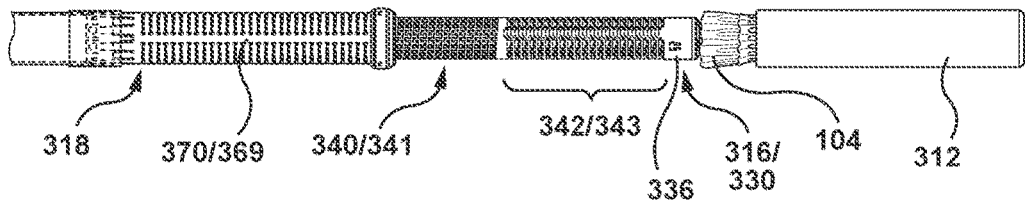
Figure 21C:
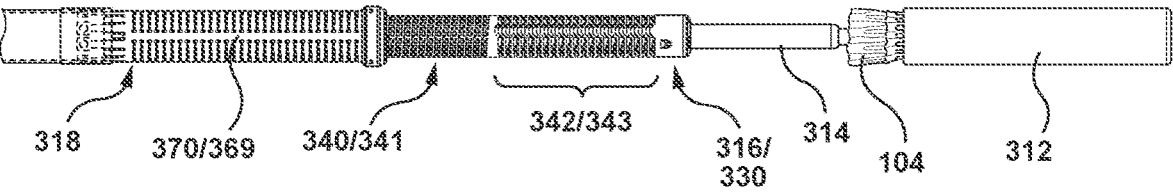

Various sequences of relative movement between the inner steerable catheter 316 and the outer steerable catheter 318 are depicted in each of FIGS. 21A-21C, 22A-22C, and 23A-23C. FIGS. 21A-21C illustrate only relative axial movement between the inner steerable catheter 316 and the outer steerable catheter 318, with each of the inner steerable catheter 316 and the outer steerable catheter 318 being in the non-flexed configuration. As described above, the subassembly of the inner steerable catheter 316 and the flexible shaft 314 is slidingly disposed within the outer steerable catheter 318 such that relative axial movement is permitted therebetween. In addition, relative axial movement is permitted between the flexible shaft 314 and the inner steerable catheter 316. The amount of relative axial movement that is permitted between the subassembly and the outer steerable catheter 318, and between the flexible shaft 314 and the inner steerable catheter 316, is limited or controlled as will be explained in more detail below. Due to the relative axial movement permitted therebetween, the inner flex component 330 has a telescoping relationship with the outer flex component 370. At least the second longitudinal portion 342 of the inner flex component 330 can telescope into and out of the outer flex component 370, regarding of whether the first longitudinal portion 340 is in its free state (i.e., floppy) or its second state (i.e., self-standing or rigid).

In FIG. 21A, the outer distal flex component 370 is disposed over the second cut pattern 343 of the inner distal flex component 370 such that the distal end 376 of the outer distal flex component 370 abuts against or is directly adjacent to the valve brim 104 of the prosthetic heart valve 100 which is contained within the distal sheath capsule 312. The outer steerable catheter 318 cannot be distally advanced beyond the position illustrated in FIG. 21A, and similarly the subassembly of the inner steerable catheter 316 and the flexible shaft 314 cannot be proximally retracted beyond the position illustrated in FIG. 21A, because the distal sheath capsule 312 abuts against or is directly adjacent to the valve brim 104 of the prosthetic heart valve 100. The configuration of FIG. 21A may be utilized when tracking the delivery system 310 through the vasculature, as independent steering or flexing of the inner steerable catheter 316 and the outer steerable catheter 318 is not yet required.

In FIG. 21B, the outer distal flex component 370 is disposed over a portion of the first cut pattern 341 of the inner distal flex component 370 and the second cut pattern 343 of the inner distal flex component 370 is exposed or not covered by the outer distal flex component 370. The distal end 336 of the inner distal flex component 330 abuts against or is directly adjacent to the valve brim 104 of the prosthetic heart valve 100 which is contained within the distal sheath capsule 312. The subassembly of the inner steerable catheter 316 and the flexible shaft 314 cannot be distally advanced beyond the position illustrated in FIG. 21B, and similarly the outer steerable catheter 318 cannot be proximally retracted beyond the position illustrated in FIG. 21B, due to contact between the distal end of the handle 317 of the inner steerable catheter 316 and the proximal end of the handle 319 of the outer steerable catheter 316. While in the configuration of FIG. 21B, because the second cut pattern 343 of the inner distal flex component 370 is exposed, the inner steerable catheter 316 may be transitioned to its flexed configuration to change the orientation of the distal capsule sheath 312 as desired. In addition, the outer steering catheter 318 may be transitioned to its flexed configuration as well to change the orientation of the distal capsule sheath 312. When outer distal flex component 370 is bent or curved by the second pullwire 390, the portion of the first longitudinal portion 340 of the inner distal flex component 330 that is disposed under the outer distal flex component 370 is concurrently bent or curved by the outer distal flex component 370.

In FIG. 21C, the flexible shaft 314 is distally advanced relative to the inner steerable catheter 316 and the outer distal flex component 370 remains disposed over a portion of the first cut pattern 341 of the inner distal flex component 370 with the second cut pattern 343 of the inner distal flex component 370 exposed. The flexible shaft 314 cannot be distally advanced beyond the position illustrated in FIG. 21C, because the amount of relative axial movement that is permitted between the flexible shaft 314 and the inner steerable catheter 316 is limited or controlled by the telescoping portion 313 at the distal end of the manifold 315 as described above. While in the configuration of FIG. 21C, because the second cut pattern 343 of the inner distal flex component 370 is exposed, the inner steerable catheter 316 may be transitioned to its flexed configuration to change the orientation of the distal capsule sheath 312 as desired. In addition, the outer steering catheter 318 may be transitioned to its flexed configuration as well to change the orientation of the distal capsule sheath 312. When outer distal flex component 370 is bent or curved by the second pullwire 390, the portion of the first longitudinal portion 340 of the inner distal flex component 330 that is disposed under the outer distal flex component 370 is concurrently bent or curved by the outer distal flex component 370.

Figure 22A:
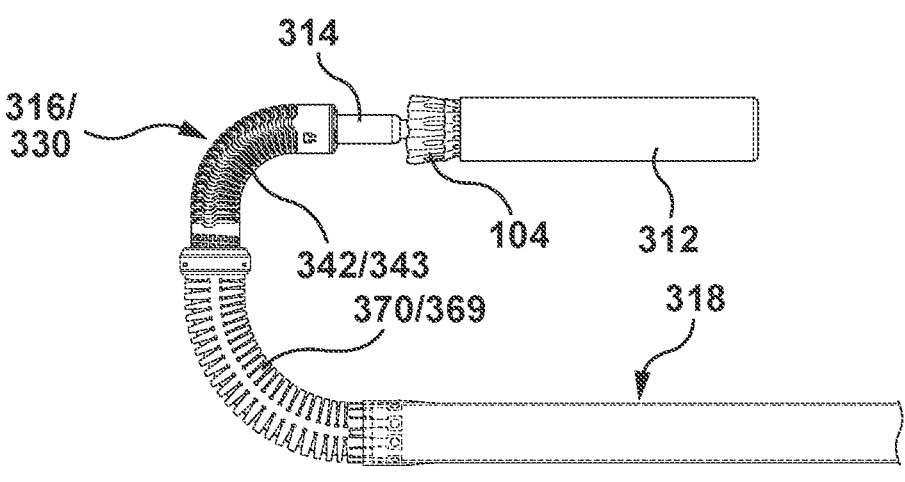
FIGS. 22A-22C illustrate relative axial movement between the inner steerable catheter and the outer steerable catheter, with each of the inner steerable catheter and the outer steerable catheter being in a flexed configuration.
Figure 22B:
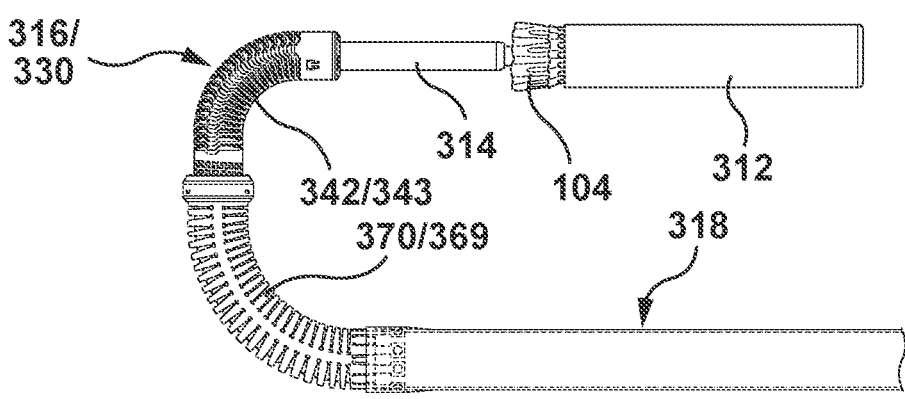
Figure 22C:
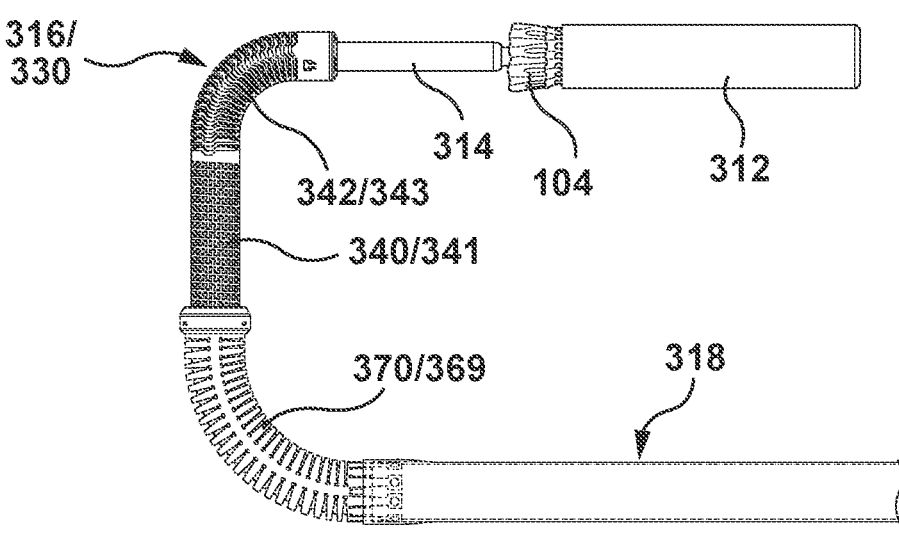

FIGS. 22A-22C illustrate relative axial movement between the inner steerable catheter 316 and the outer steerable catheter 318, with each of the inner steerable catheter 316 and the outer steerable catheter 318 being in the flexed configuration. In FIG. 22A, the outer distal flex component 370 is disposed over a portion of the first cut pattern 341 of the inner distal flex component 370 and the second cut pattern 343 of the inner distal flex component 370 is exposed or not covered by the outer distal flex component 370. Because the second cut pattern 343 of the inner distal flex component 370 is exposed, the inner steerable catheter 316 may be transitioned to its flexed configuration as shown in FIG. 22A. In addition, the outer steering catheter 318 may be transitioned to its flexed configuration as shown in FIG. 22A. With both the inner steerable catheter 316 and the outer steerable catheter 318 being in the flexed configuration, the distal portion of the delivery system 310 forms a 180° angle such that the distal sheath capsule 312 is oriented substantially parallel to the shaft 364 of the outer steerable catheter 318. Although bendability up to a 180° angle is generally preferred so that a user can orient the distal sheath capsule 312 substantially parallel to the shaft 364 of the outer steerable catheter, in another embodiment, with both the inner steerable catheter 316 and the outer steerable catheter 318 being in the flexed configuration, the distal portion of the delivery system 310 forms an angle less than 180°. Further, in an embodiment, with both the inner steerable catheter 316 and the outer steerable catheter 318 being in the flexed configuration, the distal portion of the delivery system 310 forms up to a 220° angle. Further, with the outer distal flex component 370 being disposed over most of the first cut pattern 341 of the inner distal flex component 370, the width or distance between the proximal end of the outer distal flex component 370 and the distal end of the inner distal flex component 330 is between 50 mm and 60 mm.

In FIG. 22B, the flexible shaft 314 is distally advanced relative to the inner steerable catheter 316 and the outer distal flex component 370 remains disposed over a portion of the first cut pattern 341 of the inner distal flex component 370 with the second cut pattern 343 of the inner distal flex component 370 exposed. With both the inner steerable catheter 316 and the outer steerable catheter 318 being in the flexed configuration, the distal portion of the delivery system 310 remains in the 180° angle such that the distal sheath capsule 312 is oriented substantially parallel to the shaft 364 of the outer steerable catheter 318 and the width or distance between the proximal end of the outer distal flex component 370 and the distal end of the inner distal flex component 330 remains between 50 mm and 60 mm. Thus, distal advancement of the flexible shaft 314 relative to the inner steerable catheter 316 increases the distance between the distal sheath capsule 312 and a distal end of the inner steerable catheter, which adjusts an axial or depth position of the distal sheath capsule 312 within a native heart valve in situ.

As shown in FIG. 22C, the circumferential position of the distal sheath capsule 312 in situ may be adjusted by distal advancement of the subassembly of the inner steerable catheter 316 and the flexible shaft 314 relative to the outer steerable catheter 316. With both the inner steerable catheter 316 and the outer steerable catheter 318 being in the flexed configuration, the distal portion of the delivery system 310 remains in the 180° angle such that the distal sheath capsule 312 is oriented substantially parallel to the shaft 364 of the outer steerable catheter 318. However, with the outer distal flex component 370 being disposed over a smaller portion of the first cut pattern 341 of the inner distal flex component 370, the width or distance between the proximal end of the outer distal flex component 370 and the distal end of the inner distal flex component 330 increases to between 75 mm and 85 mm. Thus, distal advancement of the subassembly of the inner steerable catheter 316 and the flexible shaft 314 relative to the outer steerable catheter 316 widens or increases the width or distance between the proximal end of the outer distal flex component 370 and the distal end of the inner distal flex component 330, which adjusts a circumferential position of the distal sheath capsule 312 within a native heart valve in situ. Notably, the curvature of the second longitudinal portion 342 of the inner distal flex component 330 may be changed without changing or substantially changing the shape or curvature of the first longitudinal portion 340 of the inner distal flex component 330. Stated another way, the second longitudinal portion 342 of the inner distal flex component 330 can bend without bending the first longitudinal portion 340 of the inner distal flex component 330. As previously described, when sufficient tension is applied to the inner distal flex component 330, the first longitudinal portion 340 transitions to its second or self-standing state while the second longitudinal portion 342 bends or curve.

FIGS. 23A-23C illustrate relative axial and rotational movement between the inner steerable catheter 316 and the outer steerable catheter 318, with each of the inner steerable catheter 316 and the outer steerable catheter 318 being in the flexed configuration. As described above, the subassembly of the inner steerable catheter 316 and the flexible shaft 314 is disposed within the outer steerable catheter 318 such that relative rotation is permitted therebetween. However, no relative rotational movement is permitted between the inner steerable catheter 316 and the flexible shaft 314. Rather, due to the handle subassembly 311, the subassembly of the inner steerable catheter 316 and the flexible shaft 314 rotate together when either of the handle 317 or the manifold 315 is rotated.

In FIG. 23A, the outer distal flex component 370 is disposed over a portion of the first cut pattern 341 of the inner distal flex component 370 and the second cut pattern 343 of the inner distal flex component 370 is exposed or not covered by the outer distal flex component 370. Because the second cut pattern 343 of the inner distal flex component 370 is exposed, the inner steerable catheter 316 may be transitioned to its flexed configuration as shown in FIG. 23A. In addition, the outer steering catheter 318 may be transitioned to its flexed configuration as shown in FIG. 23A.

From the configuration of FIG. 23A, a user may torque or rotate the subassembly of the inner steerable catheter 316 and the flexible shaft 314 in order to properly position the distal sheath capsule 312 in situ as shown in FIG. 23B. More particularly, the subassembly of the inner steerable catheter 316 and the flexible shaft 314 may be torqued or rotated while the outer steerable catheter 318 remains stationary and in its flexed configuration. While being torqued or rotated, the inner steerable catheter 316 remains in its flexed configuration unless otherwise transitioned to the non-flexed configuration. The subassembly of the inner steerable catheter 316 and the flexible shaft 314 may be rotated or torqued at least 90 degrees relative to the outer steerable catheter 318, and in an embodiment, may be rotated or torqued 360 degrees. The ability to torque or rotate the subassembly of the inner steerable catheter 316 and the flexible shaft 314 while the outer steerable catheter 318 remains stationary in the flexed configuration allows a user to change the angle or alignment of the distal sheath capsule 312 relative to the native valve in situ. Particularly, it affords the user with the ability to coaxially align the distal sheath capsule 312, and the prosthetic heart valve 100, with a native mitral heart valve prior to advancement into the native mitral heart valve, without impacting steering or placement of the outer steerable catheter 318 which may be disposed across the septum. The first cut pattern 341 of the first longitudinal portion 340 is configured to move along a 360 degrees path (via rotation of the subassembly of the inner steerable catheter 316 and the flexible shaft 314 about its axis) while still maintaining the curvature of the second cut pattern 343 of the second longitudinal portion 342 when in the flexed configuration. As a result, the exposed distal portion of the delivery system 310, including the distal sheath capsule 312 and the second longitudinal portion 342 can orbit or travel in a 360 degree path even when the second longitudinal portion 342 is in the flexed configuration. When the subassembly of the inner steerable catheter 316 and the flexible shaft 314 is continuously rotated for multiple revolutions, the distal sheath capsule 312 and the second longitudinal portion 342 can orbit or travel in multiple 360 degree revolutions as well.

Once the distal sheath capsule 312 is coaxially aligned with the native mitral heart valve as described with respect to FIG. 23B, the flexible shaft 314 is distally advanced relative to the inner steerable catheter 316 as shown in FIG. 23C. Distal advancement of the flexible shaft 314 adjusts the axial or depth position of the distal sheath capsule 312 so that the distal sheath capsule 312 may be positioned within the native mitral heart valve in situ. At this stage, the distal sheath capsule 312 is positioned as desired within the native mitral heart valve and the prosthetic heart valve 100 may be deployed.

Figure 24:
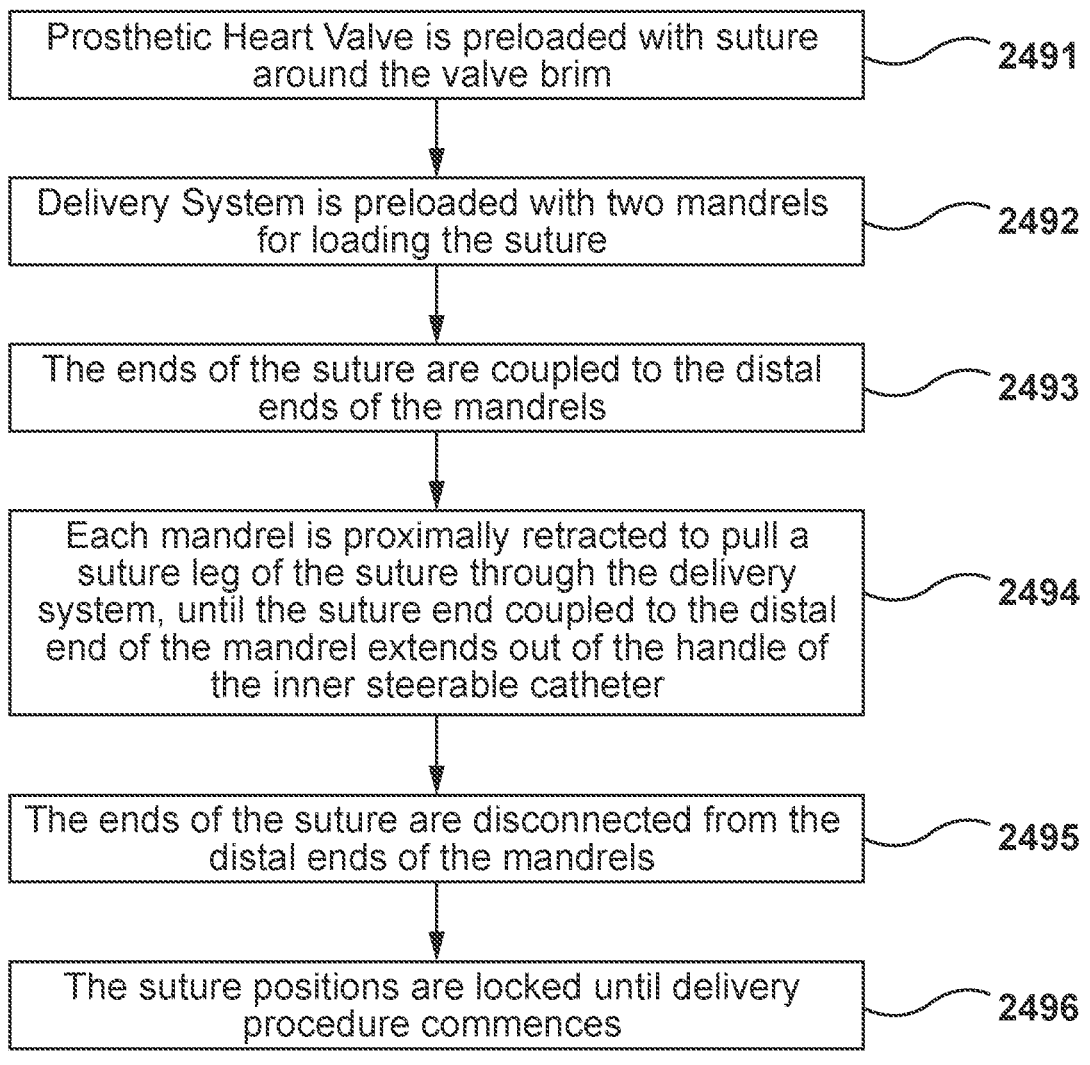
FIG. 24 shows a method of loading a suture of the prosthetic heart valve of FIG. 1 into the delivery system of FIG. 3.
Figure 25:
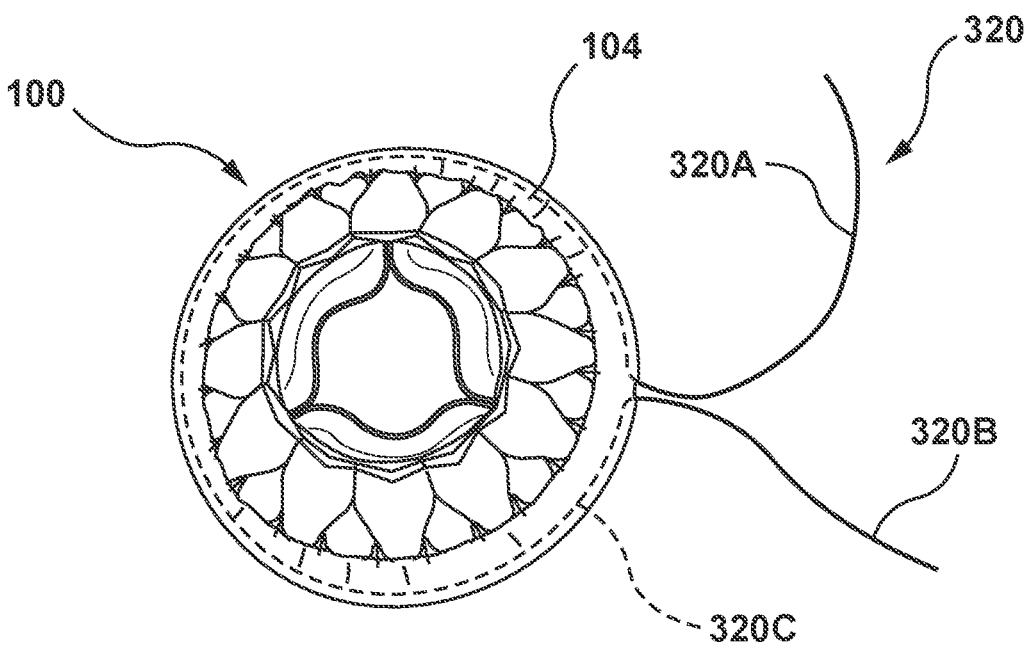
FIG. 25 illustrates the prosthetic heart valve of FIG. 1 including the suture preloaded thereon.

Turning now to FIG. 24, a method of loading the suture 320 of the prosthetic heart valve 100 into the delivery system 310 will be described. It is not necessary that the following method steps to occur in the order in which they are described. Further, throughout the method of FIG. 24, the prosthetic heart valve 100 may be hydrated using saline throughout the suture loading procedure. With reference to step 2491 in FIG. 24 as well as FIG. 25, the prosthetic heart valve 100 is preloaded, or manufactured, with the suture 320 disposed around the inflow edge of a prosthetic heart valve, which is the valve brim 104 for the prosthetic heart valve 100. More particularly, the suture 320 is disposed within the integral folded pocket or hem of the graft material 103B. As previously described, the suture 320 is a single, continuous elongated component that is described herein as integrally including the first leg 320A, the second leg 320B, and the loop 320C formed therebetween the first and second legs 320A, 320B. The portion of the suture 320 that is disposed around the valve brim 104 is the loop 320C. The loop 320C of the suture 320 encircles or extends circumferentially around the valve brim 104 of the prosthetic heart valve 100 and in an embodiment, extends circumferentially between 350 degrees and 359 degrees around the valve brim 104. In the preloaded configuration, each of the first and second legs 320A, 320B may be wrapped around a spool 2797 (shown in FIG. 27) to prevent entanglement thereof during transport and loading. Stated another way, a suture length except for the loop 320C of the suture 320 is wrapped around the spool 2797.

In another embodiment hereof, the prosthetic heart valve 100 may be preloaded, or manufactured, with a temporary suture (not shown) around the valve brim 104 that can be replaced with the suture 320 before loading the suture 320 into the delivery system 310. The temporary suture may be of a shorter length than the suture 320. A user can couple an end of the temporary suture to an end of the suture 320, and by pulling on the opposing end of the temporary suture, the suture 320 is pulled into position around the valve brim 104. The temporary suture can then be disconnected from the suture 320.

Figure 26:
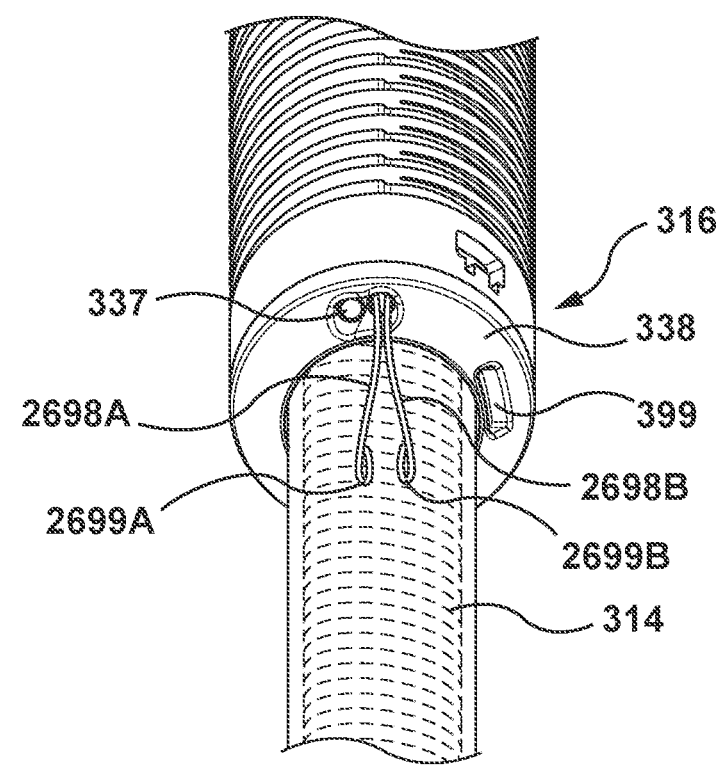
FIG. 26 illustrates the a distal portion of the delivery system of FIG. 3 with two mandrels preloaded therein.

With reference to step 2492 in FIG. 24 and FIG. 26, the delivery system 310 is preloaded, or manufactured, with two mandrels for loading the suture 320 into the delivery system 310. A first mandrel 2698A extends through the first lumen 361A of the dual lumen tube 360, and a second mandrel 2698B extends through the second lumen 361B of the dual lumen tube 360. The proximal ends (not shown) of the mandrels 2698A, 2698B extend out of the handle 317 of the inner steerable catheter 316. The distal end of the first mandrel 2698A includes a first loop or hook 2699A that is configured to grasp a first end (adjacent to the first leg 320A) of the suture 320, and the distal end of the second mandrel 2698B includes a second loop or hook 2699B that is configured to grasp a second end (adjacent to the second leg 320B) of the suture 320. In an embodiment, each of the first and second mandrels 2698A, 2698B are formed from a single, elongated wire and the hooks 2699A, 2699B are integral loops formed thereon. The terminating first and second ends of each single, elongated wire exit or extend proximally out of the handle 317, so as to be accessible to the user, and the integral loop of each single, elongated wire exits or extends distally out of the dual lumen tube 360 for grasping the respective end of the suture 320. In another embodiment, each of the first and second mandrels 2698A, 2698B may be formed from a wire component having a loop or hook attached to a distal end thereof.

To load the suture 320 into the delivery system, the first and second ends of the suture 320 are coupled to the distal ends of the mandrels 2698A, 2698B as shown in step 2493 of FIG. 24. A user attaches the first end of the suture 320 to the first mandrel 2698A by positioning the first end of the suture 320 into the first hook 2699A, and attaches the second end of the suture 320 to the second mandrel 2698B by positioning the second end of the suture 320 into the second hook 2699B.

Figure 27:
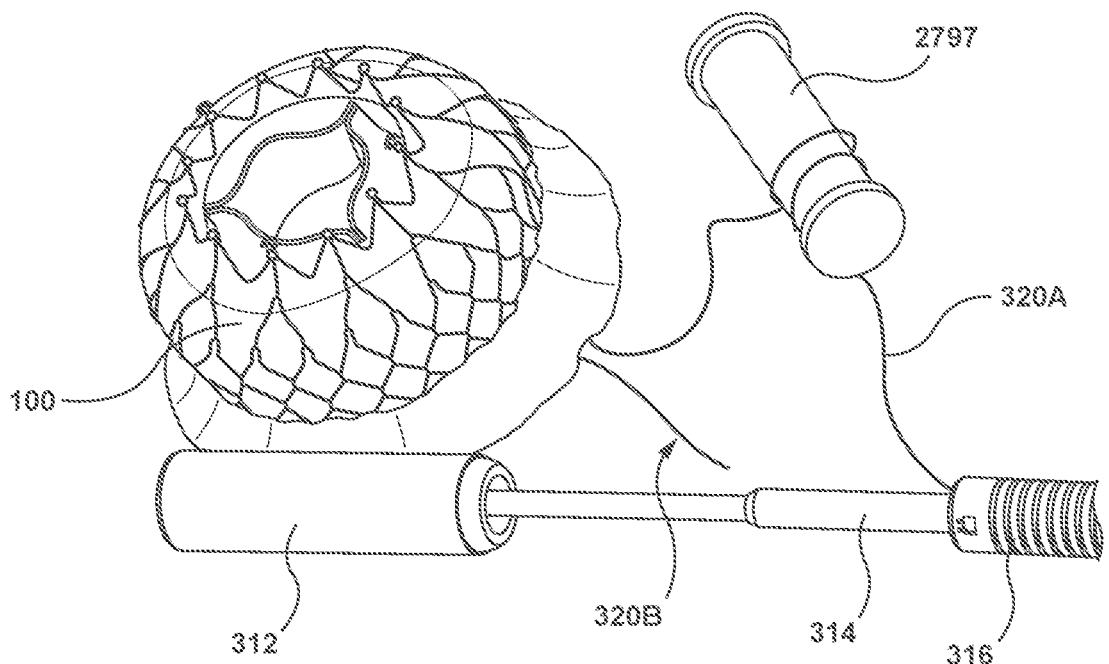
FIG. 27 illustrates pulling the suture through the delivery system of FIG. 3 with the mandrels.

With reference to step 2494 in FIG. 24 and FIG. 27, each mandrel 2698A, 2698B is proximally retracted to pull a respective suture leg 320A, 320B of the suture 320 through the dual lumen tube 360 of the delivery system 310, until the first and second ends of the suture 320 extends out of the handle 317 of the inner steerable catheter 316. The mandrels 2698A, 2698B may be proximally retracted simultaneously, or consecutively. While the mandrel is removed proximally retracted, a user may unwind or unwrap the suture legs 320A, 320B from the spool 2797 so that each suture leg 320A, 320B may be pulled into the respective lumen of the dual lumen tube 360.

Figure 28:
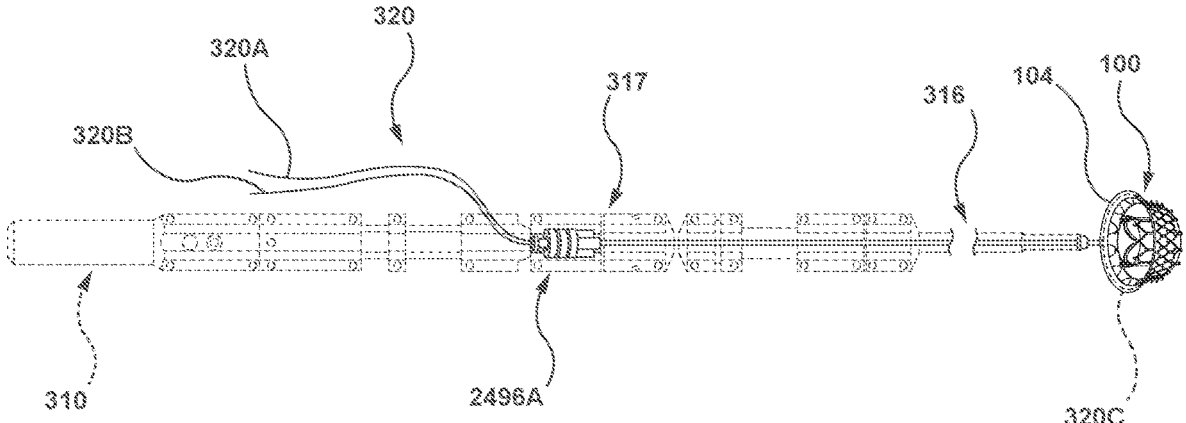
FIG. 28 illustrates a side view of the delivery system of FIG. 3 with the suture loaded therein.

With reference to step 2495 in FIG. 24 and FIG. 28, once the suture ends extend out of the handle 317 of the inner steerable catheter 316, the ends of the suture 320 are disconnected or uncoupled from the distal ends of the mandrels 2698A, 2698B. At this point in the suture loading method, the first and second ends of the suture 320 extend proximally out of the handle 317, as shown in FIG. 28, so as to be accessible to the user. The first leg 320A of the suture 320 extends through the first lumen 361A of the dual lumen tube 360, and the second leg 320B of the suture 320 extends through the second lumen 361B of the dual lumen tube 360. The loop 320C of the suture 320 still encircles or extends circumferentially around the valve brim 104 of the prosthetic heart valve 100.

With the suture 320 in place as desired, the position of the suture 320 is locked relative to the delivery system 310 until the delivery procedure commences as shown in step 2496 of FIG. 24. The handle 317 of the inner steerable catheter 316 includes a stopcock or suture lock 2496A that is configured to lock or maintain the suture 320 in its loaded position. Once the delivery procedure commences, the suture lock 2496A is unlocked to allow the delivery system 310 to be tracked through the vasculature and to allow the manipulation (i.e., axial translation and/or rotation) of the radially compressed prosthetic heart valve 100 in situ to properly position the prosthetic heart valve 100 before deployment. In an embodiment, a cradle device (not shown) such as the one disclosed in U.S. application Ser. No. 16/862,321, filed Apr. 29, 2020, receives the proximal portion of the delivery system 310 during the delivery procedure. The cradle device receives the manifold 315, the handle 317, and the handle 319 to maintain the relative positions of the flexible shaft 314, the inner steerable catheter 316, and the outer steerable catheter 318 relative to each other.

Figure 29:
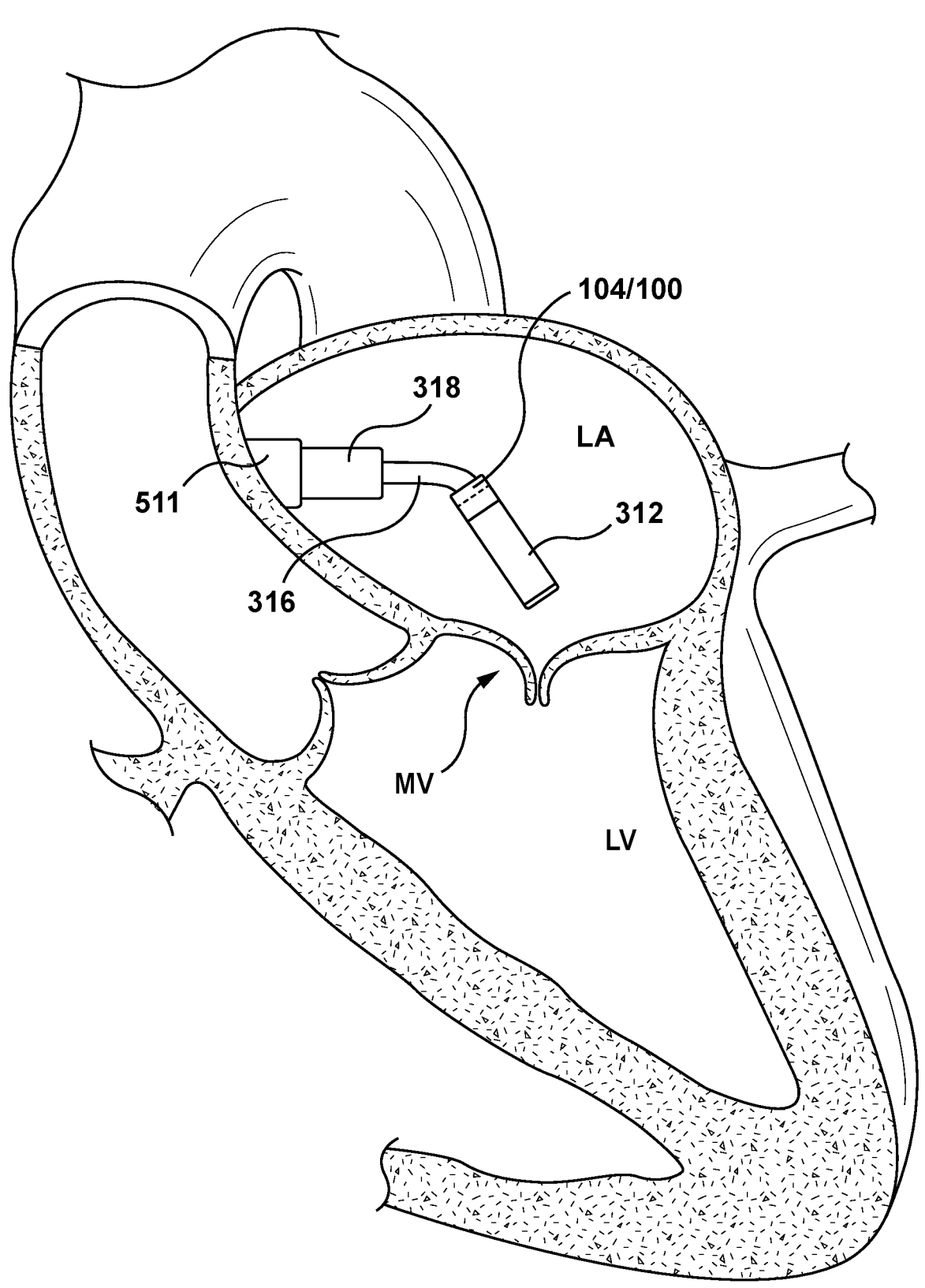
FIGS. 29-33 are sectional cut-away views of a heart illustrating a transseptal approach for delivering and positioning the prosthetic heart valve of FIG. 1 using the delivery system of FIG. 3.

FIGS. 29-33 are sectional cut-away views of a heart illustrating a transseptal approach for delivering and positioning the prosthetic heart valve 100 using the delivery system 310 and in accordance with an embodiment hereof. It is not necessary that the following operations of method of use occur in the order in which they are described. With reference to FIG. 29, the delivery system 310 is shown after having been introduced into the vasculature via a percutaneous entry point, e.g., the Seldinger technique, and having been tracked through the vasculature and into the left atrium so that distal sheath capsule 312 is positioned proximate the native mitral valve MV. Intravascular access to the right atrium RA may be achieved via a percutaneous access site to femoral venous access up to the inferior vena cava, or other known access routes. Thereafter, a guidewire (not shown) is advanced through the circulatory system, eventually arriving at the heart. The guidewire is directed into the right atrium, traverses the right atrium and is made to puncture with the aid of a transeptal needle or pre-existing hole, the atrial septum, thereby entering the left atrium LA. Once the guidewire is positioned, the endoluminal entry port and the atrial septum are dilated to permit entry of the introducer sheath 511 into the left atrium LA. Thereafter, the introducer sheath 511 is advanced over the guidewire and into the left atrium LA through the punctured atrial septum and positioned proximate or upstream to the native mitral valve MV. The guidewire is removed and the delivery system 310 is advanced through the introducer sheath 511. Although described as a transfemoral antegrade approach for percutaneously accessing the mitral valve, the prosthetic heart valve 100 may be positioned within the desired area of the heart via entry other different methods such as a transseptal antegrade approach via a thoracotomy for accessing the mitral valve. In addition, although described with the use of a guidewire, in another embodiment hereof the introducer sheath 511 may access the right atrium without the use of a guidewire.

In FIG. 29, the distal portion of delivery system 310 is shown positioned in the left atrium LA with the distal sheath capsule 312 and the loop 320C of the suture 320 concurrently holding the prosthetic heart valve 100 in a reduced diameter state. With the distal sheath capsule 312 and the loop 320C of the suture 320 holding the prosthetic heart valve 100 in a reduced diameter state, the delivery system 310 is flexible enough to bend or curve the required angle when being advanced from the atrial septum towards the native mitral valve MV. More particularly, during a transseptal approach, the distal portion of the delivery system 310 is required to bend or curve approximately 90 degrees in order to be positioned proximate to the native mitral valve MV. The relatively short distal sheath capsule 312 essentially forms a hinge point at which the distal portion of the delivery system 310 is allowed to bend or turn within the confined space of the left atrium LA. Thus, the delivery system 310 having the relatively short distal sheath capsule 312 is permitted to turn or bend more flexibly than a delivery catheter with a long, rigid capsule covering the full length of the prosthetic heart valve.

In embodiments, the introducer sheath 511 may be retracted across the septum after the distal sheath capsule 312, the inner steerable catheter 316, and the outer steerable catheter 318 have crossed the septum. Thus, the introducer sheath 511 is not shown in FIGS. 30-33.

Figure 30:
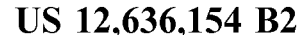

By manipulating the inner and outer distal flex components 330, 370, respectively, via the respective handles of the inner and outer steerable catheters 316, 318, outside the vasculature, a clinician may remotely manipulate and steer the distal portion of the delivery system 310 within the confined space of the left atrium LA. As shown in FIG. 30, and as previously described with respect to FIG. 24B, a user may torque or rotate the subassembly of the inner steerable catheter 316 and the flexible shaft 314 in order to properly position the distal sheath capsule 312 in situ. More particularly, the subassembly of the inner steerable catheter 316 and the flexible shaft 314 may be torqued or rotated while the outer steerable catheter 318 remains stationary and in its flexed configuration. While being torqued or rotated, the inner steerable catheter 316 remains in its flexed configuration unless otherwise transitioned to the non-flexed configuration. The rotation allows a user to change the angle or alignment of the distal sheath capsule 312 relative to the native mitral valve MV. Particularly, it affords the user with the ability to coaxially align the distal sheath capsule 312, and the prosthetic heart valve 100, with the native mitral heart valve MV prior to advancement into the native mitral heart valve, without impacting the placement of the outer steerable catheter 318 which is disposed across the septum. Although the subassembly of the inner steerable catheter 316 and the flexible shaft 314 may be rotated a full 360 degrees, it will be understood by one of ordinary skill in the art that it is not required to rotate the subassembly of the inner steerable catheter 316 and the flexible shaft 314 a full 360 degrees. The range of rotation in a valve implantation procedure may require, for example, rotation in the range of 0-90 degrees or 0-120 degrees. Accordingly, although it is preferable that the subassembly of the inner steerable catheter 316 and the flexible shaft 314 may be rotatable relative to the outer catheter a full 360 degrees, in another embodiment hereof, the subassembly of the inner steerable catheter 316 and the flexible shaft 314 is rotatable relative to the outer catheter at least 90 degrees.

Figure 31:
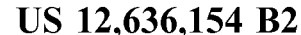

With reference to FIG. 31, and as previously described with respect to FIG. 24C, once the distal sheath capsule 312 is coaxially aligned with the native mitral heart valve MV, the flexible shaft 314 is distally advanced relative to the inner steerable catheter 316. Distal advancement of the flexible shaft 314 adjusts the axial or depth position of the distal sheath capsule 312 so that the distal sheath capsule 312 may be positioned within the annulus and/or leaflets of native mitral valve MV. The flexible shaft 314 is advanced into the left ventricle LV until the prosthetic heart valve 100 in the reduced diameter state is centered at the native mitral valve. At this stage of delivery, the distal sheath capsule 312 and the loop 320C of the suture 320 in tandem are still holding the prosthetic heart valve 100 in a reduced diameter state.

Figure 32:
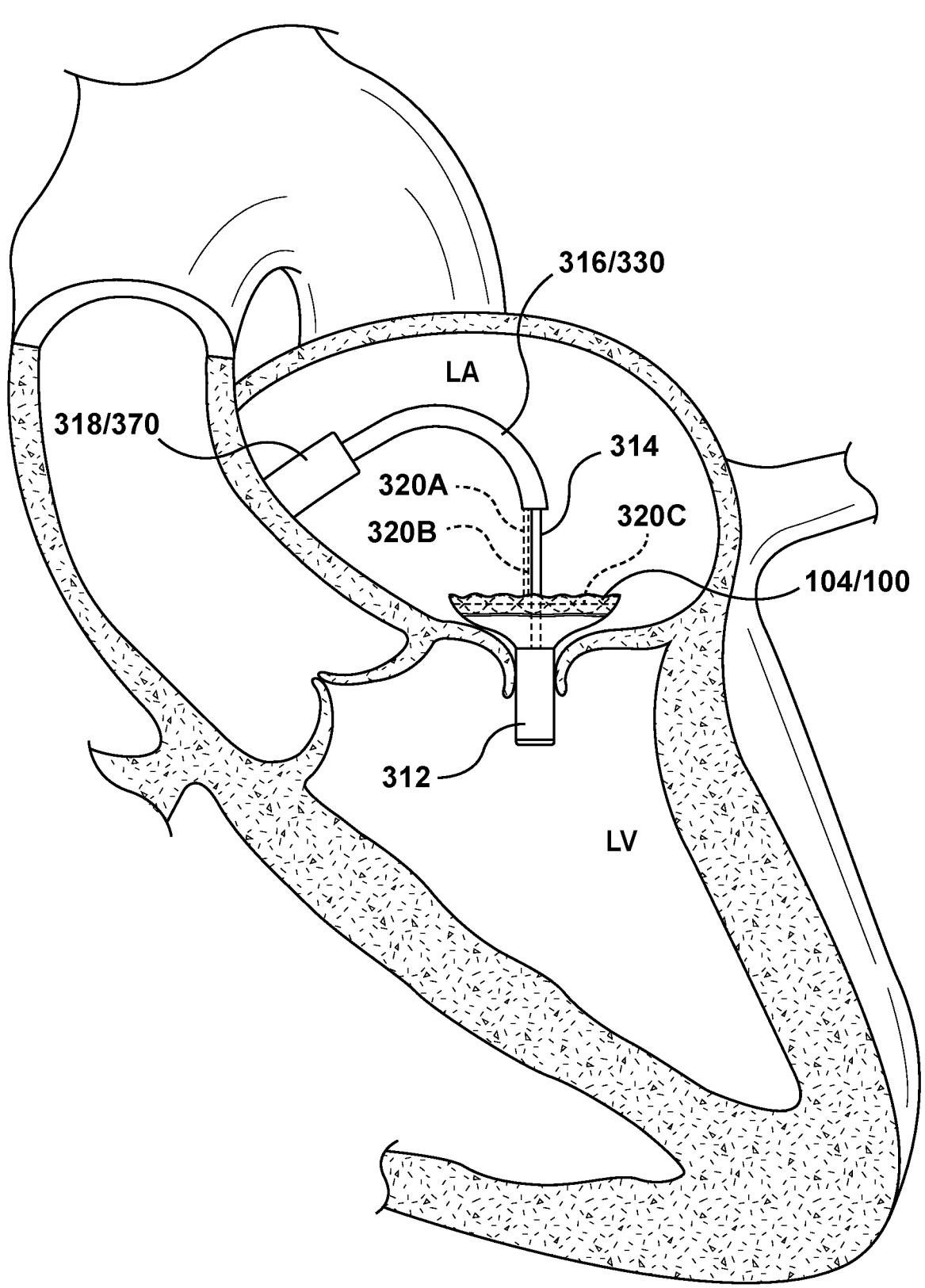

Once the prosthetic heart valve 100 is positioned within the native mitral valve MV, tension on the suture 320 is released and the valve brim 104 of the prosthetic heart valve 100 is no longer constrained in the reduced diameter state by the loop 320C of the suture 320 as shown in FIG. 32. Slack of the suture 320 permits the valve brim 104 of the prosthetic heart valve 100 to return to an expanded state within an atrial area of the native mitral valve MV. Actuation of the loop 320C of the suture 320 and subsequent deployment of the valve brim 104 of the prosthetic heart valve 100 may be considered a first stage of deployment of a two-stage deployment process for the prosthetic heart valve 100. After the valve brim 104 is radially expanded, the distal sheath capsule 312 maintains the frame 102 of the prosthetic heart valve 100 in the reduced diameter state. At this stage of deployment, the flexible shaft 314 may be axially moved relative to the inner steerable catheter 316 to finely adjust the position or height of the deployed valve brim 104 relative to the annulus of the native mitral valve. Also, although slackened, the loop 320C of the suture 320 notably still remains around the valve brim 104. Therefore, the valve brim 104 may be returned to its reduced diameter state by applying tension to the suture 320 and the valve brim 104 may be repositioned as needed.

Figure 33:
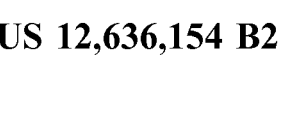

FIG. 33 is an illustration of a second stage of deployment of the prosthetic heart valve 100 in which the distal sheath capsule 312 has been distally advanced to deploy the frame 102 of the prosthetic heart valve 100. More particularly, fluid is injected through the flexible shaft 314 in order to drive the distal sheath capsule 312 distally as described above. The distal sheath capsule 312 is distally advanced to expose and release the frame 102 of the prosthetic heart valve 100, thereby permitting the frame 102 of the prosthetic heart valve 100 to return to an expanded state within an annulus of the native mitral valve MV. If the valve deployment is successful, the suture 320 is removed by pulling on one end of the suture 320 (either the end associated with the first leg 320A or the end associated with second leg 320B) until the entire suture 320 is pulled through the dual lumen tube 360 and removed from the delivery system. The introducer sheath 511 and the delivery system 310 may then be removed from the patient.

During valve deployment described above, it may become necessary to recover, recapture, or retrieve a partially deployed prosthetic heart valve 100. Such bailout procedures may become necessary when the prosthetic heart valve 100 is mislocated or damaged during deployment. After a failed valve deployment, the hydraulic system of the flexible shaft 314 may be used to draw the prosthetic heart valve 100 back into the distal sheath capsule 312 as far as possible. The valve brim 104 will protrude proximally from the distal sheath capsule 312. To ensure that the valve brim 104 can be drawn back across the septum without damage to the patient anatomy, the valve brim 104 is recaptured and returned to its reduced diameter state by applying tension to the suture 320. After the valve brim 104 has been recaptured by the suture 320 and the frame 102 has been recaptured by the distal sheath capsule 312, the outer steerable catheter 318, the inner steerable catheter 316, and the flexible shaft 314 are drawn back together into the introducer sheath 511. This may be accomplished by relative movement between the outer steerable catheter 318, the inner steerable catheter 316, and the flexible shaft 314 against the introducer sheath 511. For example, the outer steerable catheter 318, the inner steerable catheter 316, and the flexible shaft 314 may be advanced while the introducer sheath 511 is maintained in a stationary position. Alternatively, the introducer sheath 511 may be advanced while maintaining the outer steerable catheter 318, the inner steerable catheter 316, and the flexible shaft 314 in a stationary position. In another example, the outer steerable catheter 318, the inner steerable catheter 316, and the flexible shaft 314 may be retracted while the introducer sheath 511 is advanced. The introducer sheath 511 may pull the prosthetic heart valve 100 back across the septum of the patient for withdrawal without injury to patient anatomy, and the introducer sheath 511 and the delivery system 310 can be removed from the patient.

Although FIGS. 29-33 illustrate a mitral valve replacement, delivery system 310 in which distal sheath capsule 312 and the loop 320C of the suture 320 in tandem hold the prosthetic heart valve 100 in a reduced diameter state may be utilized for delivering other valve prostheses for replacement of the respective native valve such as but not limited to an aortic valve prosthesis. In addition, although the two-stage deployment process is illustrated in FIGS. 29-33 with deployment of the valve brim 104 of the prosthetic heart valve 100 deployed via slackening of the loop 320C of the suture 320 prior to deployment of the frame 102 of the prosthetic heart valve 100 deployed via distal advancement of the distal sheath capsule 312, in another embodiment hereof the distal sheath capsule 312 may be distally advanced prior to slackening of the loop 320C of the suture 320 such that the frame 102 of the prosthetic heart valve 100 is deployed prior to the valve brim 104 of the prosthetic heart valve 100. The order or sequence of the two-stage deployment is dependent upon a patient's anatomy and application, for example depending upon which valve is removed replaced (i.e., mitral, aortic, tricuspid, or pulmonary valve) and the configuration of the prosthetic heart valve.

Embodiments of the delivery system 310 include a single, continuous, releasable suture, i.e., suture 320, for radially compressing the valve brim 104. However, in another embodiment hereof (not shown), the suture 320 is eliminated and the valve brim 104 is maintained in a compressed configuration during delivery by other means, e.g., via the introducer sheath 511. Further, if the distal sheath capsule 312 crosses the septum outside of the introducer sheath 511, the septum itself may maintain compression of the protruding valve brim portion during delivery.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:
1. A delivery system for deploying a self-expanding prosthetic heart valve, comprising:
   a flexible shaft;
   a distal sheath capsule configured to contain the self-expanding prosthetic heart valve and disposed over a distal portion of the flexible shaft;
   an inner steerable catheter disposed over the flexible shaft, the inner steerable catheter including a shaft and an inner distal flex component extending from a distal end of the shaft, wherein the inner distal flex component includes a first cut pattern and a second cut pattern distal to the first cut pattern, the second cut pattern being different from the first cut pattern, the inner steerable catheter being configured to transition between a flexed configuration in which the inner distal flex component is curved along the second cut pattern and a non-flexed configuration in which the inner distal flex component is not curved along the second cut pattern; and an outer steerable catheter slidingly disposed over the inner steerable catheter, the outer steerable catheter including a shaft and an outer distal flex component extending from a distal end of the shaft, wherein the outer distal flex component includes a third cut pattern, the outer steerable catheter being configured to transition between a flexed configuration in which the outer distal flex component is curved along the third cut pattern and a non-flexed configuration in which the outer distal flex component is not curved along the third cut pattern, wherein transitioning the inner steerable catheter between the flexed and non-flexed configurations is independent from transitioning the outer steerable catheter between the flexed and non-flexed configurations, and wherein the inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

2. The delivery system of claim 1, wherein the second cut pattern of the inner distal flex component is substantially similar to the third cut pattern to the outer distal flex component.

3. The delivery system of claim 1, wherein the first cut pattern includes a plurality of generally circumferentially extending ribs separated by at least one circumferentially extending slot having a non-linear path that results in each rib of the plurality of ribs including a plurality of alternating T-shaped protrusions.

4. The delivery system of claim 1, further comprising a first pullwire extending from a first actuation mechanism of a handle of the inner steerable catheter to a distal end of the inner distal flex component, the first pullwire extending within an annular space between an inner surface of the inner steerable catheter and an outer surface of the flexible shaft, wherein tensioning of the first pullwire transitions the inner steerable catheter between the flexed and non-flexed configurations; and a second pullwire extending from a second actuation mechanism of a handle of the outer steerable catheter to a distal end of the outer distal flex component, the second pullwire extending within an annular space between an inner surface of the outer steerable catheter and an outer surface of the inner steerable catheter, wherein tensioning of the second pullwire transitions the outer steerable catheter between the flexed and non-flexed configurations.

5. The delivery system of claim 1, wherein the second cut pattern includes a plurality of generally circumferentially extending ribs separated by a plurality of generally circumferentially extending slots, each slot being circumferentially discontinuous such that the second cut pattern establishes a longitudinal spine, wherein each rib includes a curve formed thereon that extends towards a proximal end of the inner distal flex component and is configured to nest within a curve of a directly adjacent rib to form a plurality of nesting curves, the plurality of nesting curves being circumferentially opposed to the spine.

6. The delivery system of claim 5, wherein the second cut pattern further includes a plurality of cross-struts, each cross-strut extending from a curve of a rib to a directly adjacent proximal rib.

7. The delivery system of claim 1, wherein the third pattern cut pattern includes a plurality of generally circumferentially extending ribs separated by a plurality of generally circumferentially extending slots, each slot being circumferentially discontinuous such that the third cut pattern establishes a longitudinal spine, wherein each rib includes a curve formed thereon that extends towards a proximal end of the outer distal flex component and is configured to nest within a curve of a directly adjacent rib to form a plurality of nesting curves, the plurality of nesting curves being circumferentially opposed to the spine.

8. The delivery system of claim 7, wherein the third cut pattern further includes a plurality of cross-struts, each cross-strut extending from a curve of a rib to a directly adjacent proximal rib.

9. The delivery system of claim 1, wherein the inner steerable catheter is slidingly disposed over the flexible shaft such that the flexible shaft is configured to move axially relative to the inner steerable catheter.

10. The delivery system of claim 1, wherein the inner steerable catheter is rotatable 360 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

11. A delivery system comprising:

an inner steerable catheter including a shaft and an inner distal flex component extending from a distal end of the shaft, wherein the inner distal flex component includes a first cut pattern and a second cut pattern distal to the first cut pattern, the second cut pattern being different from the first cut pattern, the inner steerable catheter being configured to transition between a flexed configuration in which the inner distal flex component is curved along the second cut pattern and a non-flexed configuration in which the inner distal flex component is not curved;

an outer steerable catheter slidingly disposed over the inner steerable catheter, the outer steerable catheter including a shaft and an outer distal flex component extending from a distal end of the shaft, wherein the outer distal flex component includes a third cut pattern, the outer steerable catheter being configured to transition between a flexed configuration in which the outer distal flex component is curved along the third cut pattern and a non-flexed configuration in which the outer distal flex component is not curved;

a first pullwire extending from a first actuation mechanism of a handle of the inner steerable catheter to a distal end of the inner distal flex component, wherein tensioning of the first pullwire transitions the inner steerable catheter between the flexed and non-flexed configurations; and a second pullwire extending from a second actuation mechanism of a handle of the outer steerable catheter to a distal end of the outer distal flex component, wherein tensioning of the second pullwire transitions the outer steerable catheter between the flexed and non-flexed configurations, wherein transitioning the inner steerable catheter between the flexed and non-flexed configurations is independent from transitioning the outer steerable catheter between the flexed and non-flexed configurations, and wherein the inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

12. The delivery system of claim 11, wherein the second cut pattern of the inner distal flex component is substantially similar to the third cut pattern to the outer distal flex component.

13. The delivery system of claim 11, wherein the first cut pattern includes a plurality of generally circumferentially extending ribs separated by at least one circumferentially extending slot having a non-linear path that results in each rib of the plurality of ribs including a plurality of alternating T-shaped protrusions.

14. The delivery system of claim 11, further comprising a flexible shaft, wherein the first pullwire extends within an annular space between an inner surface of the inner steerable catheter and an outer surface of the flexible shaft, and the second pullwire extends within an annular space between an inner surface of the outer steerable catheter and an outer surface of the inner steerable catheter.

15. The delivery system of claim 11, wherein the second cut pattern includes a plurality of generally circumferentially extending ribs separated by a plurality of generally circumferentially extending slots, each slot being circumferentially discontinuous such that the second cut pattern establishes a longitudinal spine, wherein each rib includes a curve formed thereon that extends towards a proximal end of the inner distal flex component and is configured to nest within a curve of a directly adjacent rib to form a plurality of nesting curves, the plurality of nesting curves being circumferentially opposed to the spine.

16. The delivery system of claim 15, wherein the second cut pattern further includes a plurality of cross-struts, each cross-strut extending from a curve of a rib to a directly adjacent proximal rib.

17. The delivery system of claim 11, wherein the third pattern cut pattern includes a plurality of generally circumferentially extending ribs separated by a plurality of generally circumferentially extending slots, each slot being circumferentially discontinuous such that the third cut pattern establishes a longitudinal spine, wherein each rib includes a curve formed thereon that extends towards a proximal end of the outer distal flex component and is configured to nest within a curve of a directly adjacent rib to form a plurality of nesting curves, the plurality of nesting curves being circumferentially opposed to the spine.

18. The delivery system of claim 17, wherein the third cut pattern further includes a plurality of cross-struts, each cross-strut extending from a curve of a rib to a directly adjacent proximal rib.

19. The delivery system of claim 11, wherein the inner steerable catheter is rotatable 360 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration.

20. A delivery system comprising:

an inner steerable catheter including a shaft and an inner distal flex component extending from a distal end of the shaft, wherein the inner distal flex component includes a first cut pattern and a second cut pattern distal to the first cut pattern, the second cut pattern being different from the first cut pattern, the inner steerable catheter being configured to transition between a flexed configuration in which the inner distal flex component is curved along the second cut pattern and a non-flexed configuration in which the inner distal flex component is not curved; and an outer steerable catheter slidingly disposed over the inner steerable catheter, the outer steerable catheter including a shaft and an outer distal flex component extending from a distal end of the shaft, wherein the outer distal flex component includes a third cut pattern, the outer steerable catheter being configured to transition between a flexed configuration in which the outer distal flex component is curved along the third cut pattern and a non-flexed configuration in which the outer distal flex component is not curved, wherein transitioning the inner steerable catheter between the flexed and non-flexed configurations is independent from transitioning the outer steerable catheter between the flexed and non-flexed configurations, and wherein the inner steerable catheter is rotatable at least 90 degrees relative to the outer steerable catheter when the third cut pattern of the outer distal flex component is disposed over at least a portion of the first cut pattern of the inner distal flex component and each of the inner steerable catheter and the outer steerable catheter is in the flexed configuration, and wherein the first cut pattern includes a plurality of generally circumferentially extending ribs separated by at least one circumferentially extending slot having a non-linear path that results in each rib of the plurality of ribs including a plurality of alternating T-shaped protrusions.

* * * * *